(12) United States Patent
Budiman et al.

(10) Patent No.: US 12,268,844 B2
(45) Date of Patent: Apr. 8, 2025

(54) INTEGRATED INSULIN DELIVERY SYSTEM HAVING SAFETY FEATURES TO PREVENT HYPOGLYCEMIA

(71) Applicant: Abbott Diabetes Care Inc., Alameda, CA (US)

(72) Inventors: Erwin S. Budiman, Fremont, CA (US); Gary A. Hayter, Oakland, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 554 days.

(21) Appl. No.: 17/513,487

(22) Filed: Oct. 28, 2021

(65) Prior Publication Data

US 2022/0047812 A1 Feb. 17, 2022

Related U.S. Application Data

(60) Continuation of application No. 16/808,816, filed on Mar. 4, 2020, now Pat. No. 11,185,632, which is a
(Continued)

(51) Int. Cl.
*A61M 5/172* (2006.01)
*A61B 5/00* (2006.01)
(Continued)

(52) U.S. Cl.
CPC ....... *A61M 5/1723* (2013.01); *A61B 5/14532* (2013.01); *A61B 5/1495* (2013.01);
(Continued)

(58) Field of Classification Search
CPC ............ G16H 20/17; A61B 2562/0295; A61B 5/14532; A61B 5/1495; A61B 5/4839;
(Continued)

(56) References Cited

U.S. PATENT DOCUMENTS 5,569,186 A 10/1996 Lord et al.
5,665,065 A 9/1997 Colman et al.
(Continued)

FOREIGN PATENT DOCUMENTS

WO WO 99/56613 A1 11/1999
WO WO 2004/009161 A1 1/2004
(Continued)

OTHER PUBLICATIONS

Exhibit CP-6, Second Expert Report of Dr. Cesar C. Palerm, Oct. 21, 2022, Bailey, T.S et al., "Reduction in Hemoglobin A1c with Real-Time Continuous Glucose Monitoring: Results from a 12-Week Observational Study" Diabetes Technology & Therapeutics, 2007, 9(3):203-210.
(Continued)

*Primary Examiner* — Jason E Flick
(74) *Attorney, Agent, or Firm* — Sterne, Kessler, Goldstein & Fox P.L.L.C.

(57) ABSTRACT

Systems for the delivery of insulin to a patient, the system comprising: a continuous glucose sensor configured to provide a glucose level signal representative of sensed glucose; an insulin delivery device configured to deliver insulin in response to delivery control signals at a basal rate and as a bolus; and a controller programmed to receive the sensor glucose level signal and to provide a delivery control signal to an insulin delivery device to suspend a basal delivery rate during the provision of a bolus delivery and to automatically resume a preprogrammed basal delivery rate after a selected event.

20 Claims, 5 Drawing Sheets

Related U.S. Application Data continuation of application No. 16/169,350, filed on Oct. 24, 2018, now Pat. No. 10,583,251, which is a continuation of application No. 14/077,181, filed on Nov. 11, 2013, now Pat. No. 10,130,765, which is a division of application No. 13/601,944, filed on Aug. 31, 2012, now Pat. No. 8,579,854, which is a division of application No. 12/785,104, filed on May 21, 2010, now Pat. No. 8,257,300.

(60) Provisional application No. 61/180,627, filed on May 22, 2009.

(51) Int. Cl.
    *A61B 5/145*     (2006.01)
    *A61B 5/1495*    (2006.01)
    *G16H 20/17*     (2018.01)
    *A61M 5/142*     (2006.01)

(52) U.S. Cl.
    CPC ........... *A61B 5/4839* (2013.01); *G16H 20/17* (2018.01); *A61B 2562/0295* (2013.01); *A61M 2005/14208* (2013.01); *A61M 2005/14296* (2013.01); *A61M 2205/3569* (2013.01); *A61M 2205/52* (2013.01); *A61M 2230/201* (2013.01)

(58) Field of Classification Search
    CPC ......... A61M 2005/14208; A61M 2005/14296; A61M 2205/3569; A61M 2205/52; A61M 2230/201; A61M 5/1723
    See application file for complete search history.

(56) References Cited

U.S. PATENT DOCUMENTS

| | | | |
|---|---|---|---|
| 5,822,715 | A | 10/1998 | Worthington et al. |
| 6,175,752 | B1 | 1/2001 | Say et al. |
| 6,544,212 | B2 | 4/2003 | Galley et al. |
| 6,923,763 | B1 | 8/2005 | Kovatchev et al. |
| 2003/0114836 | A1 | 6/2003 | Estes et al. |
| 2005/0027463 | A1 | 2/2005 | Goode et al. |
| 2005/0038332 | A1 | 2/2005 | Saidara et al. |
| 2006/0276771 | A1 | 12/2006 | Galley et al. |
| 2007/0078314 | A1 | 4/2007 | Grounsell et al. |
| 2007/0106135 | A1 | 5/2007 | Sloan et al. |
| 2007/0149874 | A1 | 6/2007 | Say et al. |
| 2007/0173761 | A1 | 7/2007 | Kanderian et al. |
| 2007/0179370 | A1 | 8/2007 | Say et al. |
| 2007/0208244 | A1 | 9/2007 | Brauker et al. |
| 2008/0119710 | A1 | 5/2008 | Reggiardo et al. |
| 2008/0235053 | A1 | 9/2008 | Ray et al. |
| 2008/0262469 | A1 | 10/2008 | Brister et al. |
| 2008/0300572 | A1 | 12/2008 | Rankers et al. |
| 2009/0036760 | A1 | 2/2009 | Hayter |
| 2009/0055149 | A1 | 2/2009 | Hayter et al. |
| 2009/0105636 | A1* | 4/2009 | Hayter .................. G16H 40/63 604/66 |
| 2009/0192380 | A1 | 7/2009 | Shariati et al. |
| 2009/0216102 | A1 | 8/2009 | Say et al. |
| 2009/0221890 | A1 | 9/2009 | Saffer et al. |
| 2010/0161236 | A1 | 6/2010 | Cohen et al. |
| 2010/0191472 | A1 | 7/2010 | Doniger et al. |
| 2010/0198314 | A1 | 8/2010 | Wei |

FOREIGN PATENT DOCUMENTS

| | | | |
|---|---|---|---|
| WO | WO 2006/079867 | A1 | 8/2006 |
| WO | WO 2008/030347 | A2 | 3/2008 |
| WO | WO 2008/151452 | A1 | 12/2008 |
| WO | WO 2009/049252 | A1 | 4/2009 |
| WO | WO 2009/146119 | A2 | 12/2009 |

OTHER PUBLICATIONS

Exhibit CP-7, Second Expert Report of Dr. Cesar C. Palerm, Oct. 21, 2022, Garg, S. et al., "Improvement in Glycemic Excursions with a Transcutaneous, Real-Time Continuous Glucose Sensor", Diabetes Care, 2006, 29(12):44-50.

Exhibit CP-8, Second Expert Report of Dr. Cesar C. Palerm, Oct. 21, 2022, Garg, S. et al., Relationship of Fasting and Hourly Blood Glucose Levels to HbA1c Values, Diabetes Care, 2006, 6(12):2644-2649.

Exhibit CP-10, Second Expert Report of Dr. Cesar C. Palerm, Oct. 21, 2022, "Standards of Medical Care in Diabetes—2009" Position Statement, American Diabetes Association, 2009, Diabetes Care, 32(1):S13-S61.

Exhibit No. 2, to the Expert Report of Professor Nick Oliver, Sep. 20, 2022, "Note for Guidance on Clinical Investigation of Medicinal Products in the Treatment of Diabetes Mellitus," The European Agency for the Evaluation of Medicinal Products, 2002, 12 pages.

Exhibit No. 3, to the Expert Report of Professor Nick Oliver, Sep. 20, 2022, "Defining and Reporting Hypoglycemia in Diabetes", American Diabetes Association, Diabetes Care, 2005, 28(5):1245-1249.

Exhibit No. 4, to the Expert Report of Professor Nick Oliver, Sep. 20, 2022, Amiel, S. A., et al., "Hypoglycaemia in Type 2 diabetes", Diabetic Medicine, 2008, 25:245-254.

Exhibit No. 5, to the Expert Report of Professor Nick Oliver, Sep. 20, 2022, Swinnen, S.G.H.A. et al., "Changing the glucose cut-off values that define hypoglycaemia has a major effect on reported frequencies of hypoglycaemia", Diabetologia, 2009, 52:38-41.

Exhibit No. 6, to the Expert Report of Professor Nick Oliver, Sep. 20, 2022, Frier, B.M. "Defining hypoglycaemia: what level has clinical relevance?", Diabetologia, 2009, 52:31-34.

Exhibit No. 7, to the Expert Report of Professor Nick Oliver, Sep. 20, 2022, Cryer, P.E. "Preventing Hypoglycaemia: what is the appropriate glucose alert value?" Diabetologia, 2009, 53:35-37.

Exhibit No. 11, to the Expert Report of Professor Nick Oliver, Sep. 20, 2022, "The Effect of Intensive Treatment of Diabetes on the Development and Progression of Long-Term Complications in Insulin-Dependent Diabetes Mellitus" The New England Journal of Medicine, 1993, 329(14):977-986.

Exhibit No. 12, to the Expert Report of Professor Nick Oliver, Sep. 20, 2022, National Service Framework for Diabetes: Standards, Dept. of Health, 2002, 48 pages.

Exhibit No. 13, to the Expert Report of Professor Nick Oliver, Sep. 20, 2022, Amiel, S. et al., "Training in flexible, intensive insulin management to enable dietary freedom in people with type 1 diabetes: dose adjustment for normal eating (DAFNE) randomized controlled trial" BMJ, 2002, 325; 6 pages.

Exhibit No. 14, to the Expert Report of Professor Nick Oliver, Sep. 20, 2022, "Type diabetes: diagnosis and management of type 1 diabetes in children, young people and adults" National Institute for Clinical Excellence, Clinical Guideline 15, Jul. 2004, 113 pages.

Exhibit No. 20, to the Expert Report of Professor Nick Oliver, Sep. 20, 2022, "Continuous Glucose Sensors: Continuing Questions about Clinical Accuracy" Journal of Diabetes Science and Technology, 2007; 1(5):669-675.

Exhibit No. 21, to the Expert Report of Professor Nick Oliver, Sep. 20, 2022, DeVries, J.H. "Glucose Sensing Issues For the Artificial Pancreas" Journal of Diabetes Science and Technology, 2008, 2(4):732-734.

Exhibit No. 23, to the Expert Report of Professor Nick Oliver, Sep. 20, 2022, Internet Archive, WayBack Machine, Medtronic MiniMed, 2004, 20 pages.

Exhibit No. 24, to the Expert Report of Professor Nick Oliver, Sep. 20, 2022, "Glucowatch G2, Automatic Glucose Biographer and Autosensors," 2002, 70 pages.

Exhibit No. 25, to the Expert Report of Professor Nick Oliver, Sep. 20, 2022, "Guardian® REAL-Time Continuous Glucose Monitoring System, User Guide," Medtronic MiniMed, 2006, 181 pages.

Exhibit No. 26, to the Expert Report of Professor Nick Oliver, Sep. 20, 2022, "CGMS® iPro™ Continuous Glucose Recorder, User Guide," Medtronic MiniMed, 2007, 36 pages.

(56) References Cited

OTHER PUBLICATIONS

Exhibit No. 30, to the Expert Report of Professor Nick Oliver, Sep. 20, 2022, Revised specification for publication No. 2007208244A1, 2007, 170 pages.
Exhibit No. 31, to the Expert Report of Professor Nick Oliver, Sep. 20, 2022, Revised Specification for EP625, 2008, 30 pages.
Exhibit No. 32, to the Expert Report of Professor Nick Oliver, Sep. 20, 2022, Puhr, S. et al., "Real-World Hypoglycemia Avoidance with a Predictive Low Glucose Alert Does Not Depend on Frequent Screen Views", Journal of Diabetes Sciences And Technology, 2004, 14(1): 83-86.
Exhibit No. 37, to the Second Expert Report of Professor Nick Oliver, Oct. 21, 2022, Oliver, N.S., et al., "Glucose sensors: a review of current and emerging technology", Diabetic Medicine, 2009, 26:197-210.
"Dexcom's 7-Day Continuous Glucose Monitoring System," Jun. 1, 2007, https://newatlas.com/; 1 page.
U.S. Pat. No. 8,282,549 B2, Brauker et al., published Oct. 9, 2012; 73 pages; Anlage TW 2, Taylor Wessing, Statement of Defence in *Abbott* v. *Dexcom*, Opposition to EP 3782539.
STS-7 Continuous Glucose Monitoring System User's Guide, 74 pages; 2007; Anlage TW 11 D5a, Taylor Wessing, Statement of Defence in *Abbott* v. *Dexcom*, Opposition to EP 3782539.
Summary of Safety and Effectiveness Data for STS-7 Continuous Glucose Monitoring System, Notice of Approval dated May 31, 2007; 14 pages; Anlage TW 11 D5b, Taylor Wessing, Statement of Defence in *Abbott* v. *Dexcom*, Opposition to EP 3782539.
Letter from Department of Health and Human Services to DexCom Inc. regarding STS-7 Continuous Glucose Monitoring System, dated May 31, 2007; 95 pages; Anlage TW 25, Taylor Wessing, Statement of Defence in *Abbott* v. *Dexcom*, Opposition to EP 3782539.
PMA Approvals FDA—webpage available at: https://www.fda.gov; 3 pages, accessed Sep. 14, 2022.
PMA database search for Freestyle Navigator Continuous Glucose Monitor—https://www.fda.gov; 6 pages, accessed Sep. 14, 2022.
Getting Started with CareLink Personal Software Continuous Glucose Monitoring; Medtronic, 2009, 28 pages.
Sparacino, Giovanni et al., "Glucose Concentration can be Predicted Ahead in Time From Continuous Glucose Monitoring Sensor Time-Series," IEEE Transactions on Biomedical Engineering, Vo. 54, No. 5, May 2007; 7 pages.
Sandham, William et al., "Blood Glucose Prediction for Diabetes Therapy Using a Recurrent Artificial Neural Network," 9th European Signal Processing Conference (EUSIPCO 1998), 1998, pp. 1-4.
FreeStyle Navigator Continuous Glucose Monitoring System, User's Guide, Abbott Diabetes Care Inc., May 2008; 195 pages.
Webpage showing FDA Premarket Approval Order for the STS-7 Continuous Glucose Monitoring System, decision date May 31, 2007; 3 pages.
Wayback Machine Internet Archive of US FDA CDRH Premarket Approval Final Decisions Rendered for May 2007; 21 pages.
Wayback Machine Internet Archive of US FDA CDRH Premarket Approval for STS-7 Continuous Glucose Monitoring System, Approved May 31, 2007; 1 page.
Kowalski, Erin J., Can We Really Close the Loop and How Soon? Accelerating the Availability of an Artificial Pancreas: A Roadmap to Better Diabetes Management, Diabetes Technology & Therapeutics, vol. 11, Supplement 1, 2009; 8 pages.

\* cited by examiner

INTEGRATED INSULIN DELIVERY SYSTEM HAVING SAFETY FEATURES TO PREVENT HYPOGLYCEMIA

CROSS-REFERENCES TO RELATED APPLICATIONS

This application is a continuation of U.S. application Ser. No. 16/808,816 filed Mar. 4, 2020 and now allowed and published as U.S. 2020/0197607, which is a continuation of U.S. application Ser. No. 16/169,350 filed Oct. 24, 2018 and now U.S. Pat. No. 10,583,251, which is a continuation of U.S. application Ser. No. 14/077,181 filed Nov. 11, 2013 and now U.S. Pat. No. 10,130,765, which is a division of U.S. application Ser. No. 13/601,944 filed Aug. 31, 2012 and now U.S. Pat. No. 8,579,854, which is a division of U.S. application Ser. No. 12/785,104 filed May 21, 2020 and now U.S. Pat. No. 8,257,300, and claims the benefit of U.S. App. 61/180,627 filed May 22, 2009.

This application is also related to U.S. Publication 2010/0317952 entitled "Methods For Reducing False Hypoglycemia Alarm Occurrence," (U.S. Provisional No. 61/180,700, filed May 22, 2009); U.S. Publication 2010/0295686 entitled "Usability Features For Integrated Insulin Delivery System," (U.S. Application 61/180,649, filed May 22, 2009); U.S. Publication 2011/0130746 entitled "Safety Layer For Integrated Insulin Delivery System," (U.S. Provisional Application 61/180,774, filed May 22, 2009); and U.S. Publication 2010/0298685 entitled "Adaptive Insulin Delivery System," (U.S. Provisional Application 61/180,767, filed May 22, 2009).

BACKGROUND

The invention is directed to an integrated system of glucose level detection and use of that information in setting insulin delivery parameters.

Diabetes is a metabolic disorder that afflicts tens of millions of people throughout the world. Diabetes results from the inability of the body to properly utilize and metabolize carbohydrates, particularly glucose. Normally, the finely-tuned balance between glucose in the blood and glucose in bodily tissue cells is maintained by insulin, a hormone produced by the pancreas which controls, among other things, the transfer of glucose from blood into body tissue cells. Upsetting this balance causes many complications and pathologies including heart disease, coronary and peripheral artery sclerosis, peripheral neuropathies, retinal damage, cataracts, hypertension, coma, and death from hypoglycemic shock In patients with insulin-dependent diabetes, the symptoms of the disease can be controlled by administering additional insulin (or other agents that have similar effects) by injection or by external or implantable insulin pumps. The "correct" insulin dosage is a function of the level of glucose in the blood. Ideally, insulin administration should be continuously readjusted in response to changes in glucose level. In diabetes management, "insulin" instructs the body's cells to take in glucose from the blood. "Glucagon" acts opposite to insulin, and causes the liver to release glucose into the blood stream. The "basal rate" is the rate of continuous supply of insulin provided by an insulin delivery device (pump). The "bolus" is the specific amount of insulin that is given to raise blood concentration of the insulin to an effective level when needed (as opposed to continuous).

Presently, systems are available for monitoring glucose levels by implanting a glucose sensitive probe into the patient. Such probes measure various properties of blood or other tissues, including optical absorption, electrochemical potential, and enzymatic products. The output of such sensors can be communicated to a hand held device that is used to calculate an appropriate dosage of insulin to be delivered into the blood stream in view of several factors, such as a patient's present glucose level, insulin usage rate, carbohydrates consumed or to be consumed and exercise, among others. These calculations can then be used to control a pump that delivers the insulin, either at a controlled basal rate, or as a bolus. When provided as an integrated system, the continuous glucose monitor, controller, and pump work together to provide continuous glucose monitoring and insulin pump control.

Such systems at present require intervention by a patient to calculate and control the amount of insulin to be delivered. However, there may be periods when the patient is not able to adjust insulin delivery. For example, when the patient is sleeping, he or she cannot intervene in the delivery of insulin, yet control of a patient's glucose level is still necessary. A system capable of integrating and automating the functions of glucose monitoring and controlled insulin delivery would be useful in assisting patients in maintaining their glucose levels, especially during periods of the day when they are unable to intervene.

What has been needed, and heretofore unavailable, is an integrated, automated system combining continuous glucose monitoring and controlled insulin delivery. Such a system would include various features to insure the accuracy of the glucose monitor and to protect the user from either under- or over-dosage of insulin. The system would include various functions for improving the usability, control, and safety of the system, including a variety of alarms which could be set by a user or a technician to avoid false alarms while ensuring adequate sensitivity to protect the user. The present invention fulfills these, and other needs.

SUMMARY OF THE INVENTION

In accordance with aspects of the invention, there is provided a system for the delivery of insulin to a patient, the system comprising a continuous glucose sensor configured to provide a sensor glucose level signal representative of sensed glucose, the sensor having a nominal sensor sensitivity, an insulin delivery device configured to deliver insulin to a patient in response to control signals, and a controller programmed to receive the sensor glucose level signal, receive the nominal sensor sensitivity, and receive a sensor sensitivity measurement, and to provide and adjust a delivery control signal to the delivery device as a function of the sensor glucose level signal and the comparison of the sensor sensitivity measurement with the nominal sensor sensitivity.

In more detailed aspects, the controller further comprises one or more safety-oriented components in the controller that modifies its control behavior as a function of estimated calibration accuracy. The controller estimates the calibration accuracy based on present and past data from the current sensor wear as well as past offline data. A safety-oriented component attempts to detect a sensor calibration anomaly and make appropriate adjustment to one or more aspects of the controller, such as the controller's target glucose range limits, the variance of one or more glucose state estimates, the variance of one or more glucose sensor measurement channels, a calibration correction factor to be used in conjunction with a sensor's signal, the decision to request a recalibration, and the decision to terminate closed-loop operation.

In other aspects, there is provided a system for the delivery of insulin to a patient, the system comprising a continuous glucose sensor configured to provide a sensor glucose level signal representative of sensed glucose an insulin delivery device configured to deliver insulin to a patient in response to control signals at a basal rate and as a bolus and a controller programmed to receive the sensor glucose level signal and to provide a delivery control signal to the delivery device to suspend a basal delivery rate during the provision of a bolus delivery and to automatically resume a preprogrammed basal delivery rate after a selected event.

In further detailed aspects, the delivery signal comprises automatic resumption of the basal delivery rate after the event of termination of the bolus rate, the delivery signal comprises automatic resumption of the basal delivery rate after the event of a certain period of time, and the delivery signal comprises automatic resumption of the basal delivery rate after consideration of the insulin on board.

In other aspects, there is provided a system for the delivery of insulin to a patient, the system comprising a continuous glucose sensor configured to provide a sensor glucose level signal representative of sensed glucose, an insulin delivery device configured to deliver insulin to a patient in response to control signals at a basal rate and as a bolus, and a controller programmed to receive the sensor glucose level signal and to provide a delivery control signal to the delivery device according to a model, that model including a monitor on the lower level of insulin over the course of time such that if the control signal were to reduce the insulin below a threshold or terminate insulin delivery, the model intervenes within a reasonable duration to cause a further action to avoid hypoglycemia.

In more detailed aspects, the model intervenes until the risk of over-compensating in the opposite direction is determined to be higher than not intervening. The model intervenes within a reasonable duration but when the reasonable duration is exceeded and the model suggests that the risk level is still unacceptable, the model considers taking another action, such as recalibration or the termination of full or partial system automation.

In another aspect, there is provided a system for the delivery of insulin to a patient, the system comprising a continuous glucose sensor configured to provide a sensor glucose level signal representative of sensed glucose, an insulin delivery device configured to deliver insulin to a patient in response to control signals at a basal rate and as a bolus, and a controller programmed to receive the sensor glucose level signal and to provide a delivery control signal to the delivery device to deliver insulin that accounts for an asymmetrical bias range of the glucose sensor such that inaccuracy in the sensor may be tolerated with limited hyperglycemia while avoiding hypoglycemia.

In yet a further aspect, there is provided a system for the delivery of insulin to a patient, the system comprising a continuous glucose monitor configured to provide a glucose level signal representative of sensed glucose, an insulin delivery device configured to deliver insulin to a patient in response to control signals, and a controller programmed to provide control signals to the delivery device to result in a basal rate of delivery and bolus delivery, the controller also programmed to receive the glucose level signal and indicate recommended changes to the delivery of insulin and/or alter the delivery as a function of glucose level signals.

In more detailed aspects, the controller provides control signals to alter the delivery of insulin based on a glucose level signal indicating existing, imminent, or a trend toward carbohydrate deficiency. Further, the controller provides control signals to terminate an extended bolus and terminate a temporary basal rate that exceeds a programmed basal rate, in response to a glucose signal indicating existing or imminent carbohydrate deficiency. Additionally, the controller provides control signals to terminate a programmed basal rate and alter future basal delivery in response to a glucose signal indicating existing or imminent carbohydrate deficiency, and the controller receives the glucose signal, informs of the trend toward carbohydrate deficiency, and indicates an option of consuming carbohydrates to alter the trend.

In another aspect, the present invention includes a system for the delivery of insulin to a patient, the system comprising a continuous glucose sensor configured to provide a glucose level signal representative of sensed glucose, the sensor having a nominal sensor sensitivity; an insulin delivery device configured to deliver insulin to a patient in response to delivery control signals; and a controller programmed to receive the glucose level signal, receive the nominal sensor sensitivity, and receive a sensor sensitivity measurement, and to determine a delivery control signal to control the delivery device in accordance with the sensor glucose level signal and a comparison of the sensor sensitivity measurement with the nominal sensor sensitivity.

In one alternative aspect, the controller further comprises one or more safety-oriented components programmed in the controller by software commands that modifies the control behavior of the processor such that the behavior of the processor is a function of estimated sensor calibration accuracy. In another alternative aspect, the controller estimates the sensor calibration accuracy based on present and past data from the glucose sensor as well as past offline data.

In yet another alternative aspect, a safety-oriented component programmed in the processor by software commands detects a sensor calibration anomaly and adjusts at least one parameter selected from the list of parameters consisting of target glucose range limits, a variance of one or more glucose state estimates, a variance of one or more glucose sensor measurement channels, a calibration correction factor to be used in conjunction with the glucose sensor's glucose level signal, a decision by the processor based upon data available from the glucose sensor and at least one other selected parameter value to request a recalibration, and a decision by the processor based upon data available from the glucose sensor and at least one other selected parameter value to terminate closed-loop operation.

In a further aspect, the present invention includes a system for the delivery of insulin to a patient, the system comprising a continuous glucose sensor configured to provide a glucose level signal representative of sensed glucose; an insulin delivery device configured to deliver insulin in response to delivery control signals at a basal rate and as a bolus; and a controller programmed to receive the sensor glucose level signal and to provide a delivery control signal to an insulin delivery device to suspend a basal delivery rate during the provision of a bolus delivery and to automatically resume a preprogrammed basal delivery rate after a selected event.

In one alternative aspect, the delivery control signal comprises automatic resumption of the basal delivery rate after termination of the bolus rate. In another alternative aspect, the delivery control signal comprises automatic resumption of the basal delivery rate after a selected period of time has elapsed since termination of the basal delivery rate. In still another alternative aspect, the delivery control signal comprises automatic resumption of the basal delivery rate after comparison of a value of insulin on board as determined by the processor to a selected threshold value for insulin on board stored in a memory in operable communication with the processor.

In yet another aspect, the present invention includes a system for the delivery of insulin to a patient, the system comprising a continuous glucose sensor configured to provide a glucose level signal representative of sensed glucose; an insulin delivery device configured to deliver insulin in response to delivery control signals at a basal rate and as a bolus; and a controller programmed to receive the sensor glucose level signal and to provide a delivery control signal to the insulin delivery device according to a model, the model including a monitor on the lower level of insulin over the course of time such that if the delivery control signal reduces the insulin delivery below a threshold or terminates insulin delivery, the processor model programming of the processor results in an intervention in the delivery of insulin by the pump to avoid hypoglycemia.

In more detailed aspects, the model programming of the processor results in an intervention in the delivery of insulin until the risk of over-compensating in an opposite direction is determined to be higher than not intervening in the insulin delivery. In a still more detailed aspect, the model programming of the processor results in an intervention of the insulin delivery within a selected duration but when the selected duration is exceeded and the model programming of the processor suggests that the risk level is still unacceptable, the model programming of the processor evaluates taking another action, such as recalibration or termination of full or partial system automation.

In another aspect, the present invention includes a system for the delivery of insulin to a patient, the system comprising a continuous glucose sensor configured to provide a glucose level signal representative of sensed glucose; an insulin delivery device configured to deliver insulin to a patient in response to delivery control signals at a basal rate and as a bolus; and a controller programmed to receive the sensor glucose level signal and to provide a delivery control signal to the insulin delivery device to deliver insulin in a manner that accounts for an asymmetrical bias range of the glucose sensor such that inaccuracy in the sensor may be tolerated with limited hyperglycemia while avoiding hypoglycemia.

In yet a further aspect, the present invention includes a system for the delivery of insulin to a patient, the system comprising a continuous glucose monitor configured to provide a glucose level signal representative of sensed glucose; an insulin delivery device configured to deliver insulin to a patient in response to delivery control signals; and a controller programmed to provide control signals to the delivery device to result in a basal rate of delivery and bolus delivery, the controller also programmed to receive the glucose level signal and to indicate recommended changes to the delivery of insulin and/or alter the delivery of insulin as a function of the glucose level signals.

In a more detailed aspect, the controller provides delivery control signals to alter the delivery of insulin based on a glucose level signal indicating existing, imminent, or a trend toward carbohydrate deficiency.

In another more detailed aspect, the controller provides delivery control signals to terminate an extended bolus and to terminate a temporary basal rate that exceeds a programmed basal rate in response to a glucose signal indicating existing or imminent carbohydrate deficiency. In still another more detailed aspect, the controller provides delivery control signals to terminate a programmed basal rate and alter future basal delivery of insulin in response to a glucose signal indicating existing or imminent carbohydrate deficiency.

In yet another more detailed aspect, the controller receives the glucose level signal from the sensor; informs a patient of a trend in the patient's glucose level toward carbohydrate deficiency; and indicates an option of consuming carbohydrates to alter the trend to the patient.

The features and advantages of the invention will be more readily understood from the following detailed description which should be read in conjunction with the accompanying drawings.

DETAILED DESCRIPTION OF THE PREFERRED EMBODIMENTS

For the purposes of promoting an understanding of the principles of the invention, reference will now be made to a number of illustrative embodiments shown in the attached drawings and specific language will be used to describe the same. It will be understood that throughout this document, the terms "user" and "patient" are used interchangeably.

Figure 1:
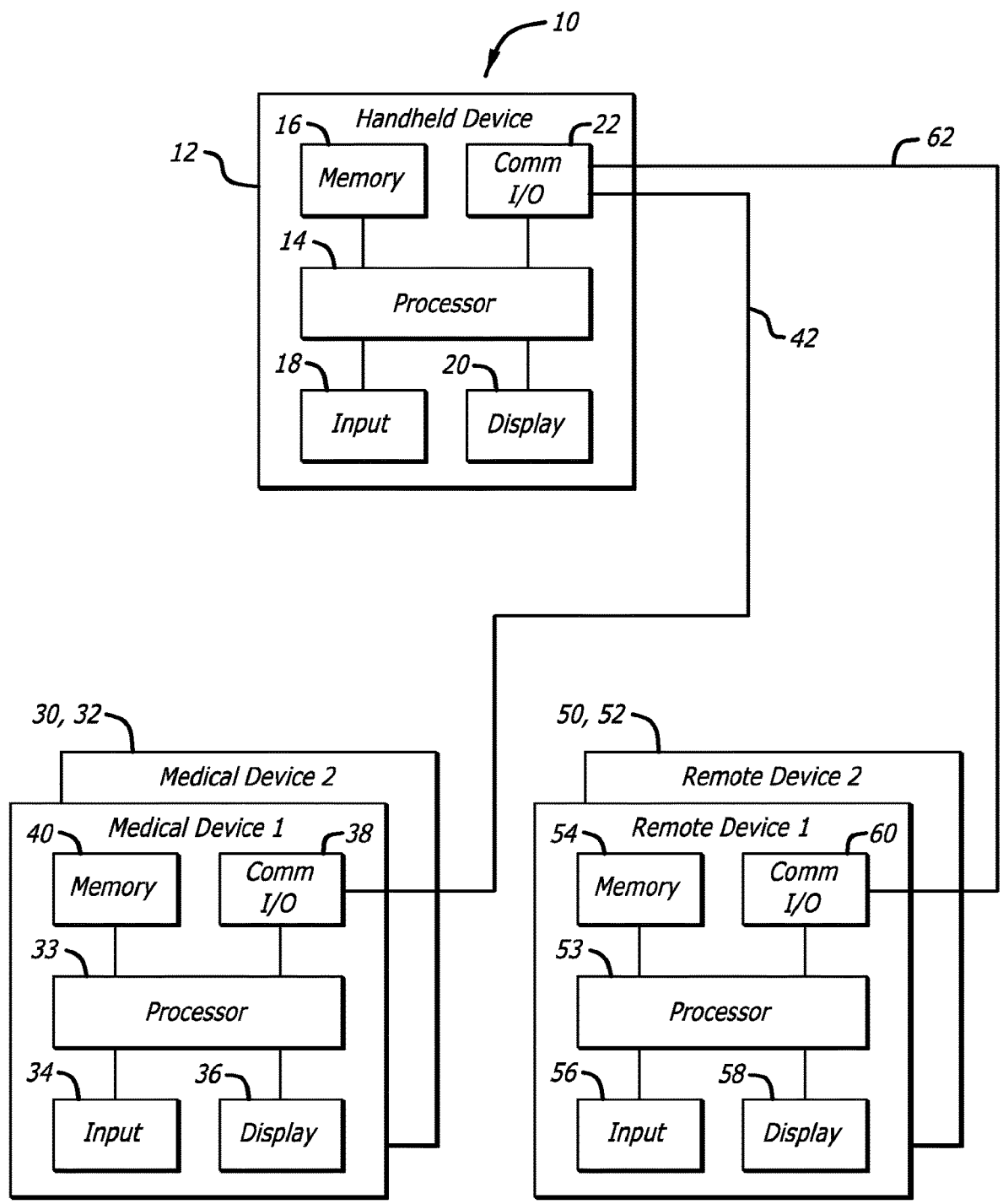
FIG. 1 is a schematic diagram illustrating an exemplary embodiment of an electronic device and its various components in operable communication with one or more medical devices, such as a glucose monitor or drug delivery pump, and optionally, in operable communication with a remote computing device.

Referring now to FIG. 1, a block diagram of one illustrative embodiment of a system 10 for monitoring, determining and/or providing drug administration information is shown. In the illustrated embodiment, the system 10 includes an electronic device 12 having a processor 14 in data communication with a memory unit 16, an input device 18, a display 20, and a communication input/output unit 24. The electronic device 12, which may be handheld, may be provided in the form of a general purpose computer, central server, personal computer (PC), laptop or notebook computer, personal data assistant (PDA) or other hand-held device, external infusion pump, glucose meter, analyte sensing system, or the like. The electronic device 12 may be configured to operate in accordance with one or more operating systems including for example, but not limited to, WINDOWS, Unix, LINUX, BSD, SOLARIS, MAC OS, or, an embedded OS such as ANDROID, PALM OS, WEBOS, eCOS, QNX, or WINCE, and may be configured to process data according to one or more internet protocols for example, but not limited to, NetBios, TCP/IP and APPLETALK. The processor 14 is microprocessor-based, although the processor 14 may be formed of one or more general purpose and/or application specific circuits and operable as described hereinafter. The memory unit 16 includes sufficient capacity to store operational data, one or more software algorithms executable by the processor 14, and other user inputted data. The memory unit 16 may include one or more memory or other data storage devices.

Display 20 is also included for viewing information relating to operation of the device 12 and/or system 10. Such a display may be a display device including for example, but not limited to, a light emitting diode (LED) display, a liquid crystal display (LCD), a cathode ray tube (CRT) display, or the like. Additionally, display 20 may include an audible display configured to communicate information to a user, another person, or another electronic system having audio recognition capabilities via one or more coded patterns, vibrations, synthesized voice responses, or the like. Additionally, display 20 may include one or more tactile indicators configured to display tactile information that may be discerned by the user or another person.

Input device 18 may be used in a manner to input and/or modify data. Input device 18 may include a keyboard or keypad for entering alphanumeric data into the processor 14. Such a keyboard or keypad may include one or more keys or buttons configured with one or more tactile indicators to allow users with poor eyesight to find and select an appropriate one or more of the keys, and/or to allow users to find and select an appropriate one or more of the keys in poor lighting conditions. Additionally, input device 18 may include a mouse or other point and click device for selecting information presented on the display 20. Additionally, input device 18 may include display 20, configured as a touch screen graphical user interface. In this embodiment, the display 20 includes one or more selectable inputs that a user may select by touching an appropriate portion of the display 20 using an appropriate implement.

Input device 18 may also include a number of switches or buttons that may be activated by a user to select corresponding operational features of the device 12 and/or system 10. Input device 18 may also be or include voice-activated circuitry responsive to voice commands to provide corresponding input data to the processor 14. The input device 18 and/or display 20 may be included with or separate from the electronic device 12.

System 10 may also include a number of medical devices 30 which carry out various functions, for example, but not limited to, monitoring, sensing, diagnostic, communication and treatment functions. In such embodiments, any of the one or more of the medical devices 30, 32 may be implanted within the user's body, coupled externally to the user's body (such as, for example, an infusion pump), or separate from the user's body. In some embodiments, medical devices 30, 32 are controlled remotely by electronic device 12. Additionally, one or more of the medical devices may be mounted to and/or form part of the electronic device 12. For example, in some embodiments, electronic device 12 includes an integrated glucose meter or strip port and is configured to receive a signal representative of a glucose value and display the value to a user. Electronic device 12 may further be configured to be used to calibrate a continuous glucose monitor (CGM) or for calculating insulin amounts for bolus delivery. Typically, the medical devices 30, 32 are each configured to communicate wirelessly with the communication I/O unit 22 of the electronic device 12 via one of a corresponding number of wireless communication links. Wireless communication is preferable when medical devices 30, 32 are configured to be located on a remote part of the body, for example, in an embodiment wherein medical device 30, 32 is a continuous glucose monitor (CGM) or sensor, or insulin pump, worn under clothing.

Electronic device 12 communicates with medical device 30, 32 via a wireless protocol, or, in some embodiments, is directly connected via a wire. The wireless communications between the various components of the system 10 may be one-way or two-way. The form of wireless communication used may include, but should not be limited to, radio frequency (RF) communication, infrared (IR) communication, Wi-Fi, RFID (inductive coupling) communication, acoustic communication, capacitive signaling (through a conductive body), galvanic signaling (through a conductive body), BLUETOOTH, or the like. Electronic device 12 and each of the medical devices 30 include circuitry for conducting such wireless communications circuit. In another embodiment, one or more of the medical devices 30, 32 may be configured to communicate with electronic device 12 via one or more serial or parallel configured hardwire connections therebetween.

Each of the one or more medical devices 30, 32 may include one or more of a processing unit 33, input 34 or output 36 circuitry and/or devices, communication ports 38, and/or one or more suitable data and/or program storage devices 40. It may be understood that not all medical devices 30, 32 will have the same componentry, but rather will only have the components necessary to carry out the designed function of the medical device. For example, in one embodiment, a medical device 30, 32 may be capable of integration with electronic device 12 and thus omit input 34, display 36, and/or processor 33. In another embodiment, medical device 30, 32 is capable of stand-alone operation, and is further configured to function as electronic device 12, should communication with electronic device 12 be interrupted. In another embodiment, medical device 30, 32 may include processor, memory and communication capability, but does not have an input 34 or a display 36. In still another embodiment, the medical device 30, 32 may include an input 34, but lack a display 36.

In some embodiments, the system 10 may additionally include a remote device or devices 50, 52. The remote device 50, 52 may include a processor 53, which may be identical or similar to the processor 33 or processor 14, a memory or other data storage unit 54, a input device 56, which may include any one or more of the input devices described hereinabove, a display unit 58 which may include any one or more of the display units described hereinabove, and a communication I/O circuitry 60. The remote device 50, 52 may be configured to communicate with the electronic device 12 or medical devices(s) 30, 32 via any wired or wireless communication interface 62, which may include any of the communication interfaces or links described hereinabove. Although not specifically shown, remote device 50, 52 may also be configured to communicate directly with one or more medical devices 30, 32, instead of communicating with the medical device through electronic device 12.

System 10 may be provided in any of a variety of configurations, and examples of some such configurations will now be described. It will be understood, however, that the following examples are provided merely for illustrative purposes, and should not be considered limiting in any way. Those skilled in the art may recognize other possible implementations of a fully closed-loop, semi closed-loop, or open loop diabetes control arrangement, and any such other implementations are contemplated by this disclosure.

In a first exemplary implementation of the system 10, the medical device 32 is provided in the form of an insulin pump 32 configured to be worn externally to the user's body and also configured to controllably deliver insulin to the user's body. The various medical devices 30, 32 may additionally include one or more sensors or sensing systems that are external to the user's body and/or sensor techniques for providing information relating to the physiological condition of the user. Examples of such sensors or sensing systems may include, but should not be limited to, a glucose strip sensor/meter, a body temperature sensor, a blood pressure sensor, a heart rate sensor, one or more bio-markers configured to capture one or more physiological states of the body, such as, for example, HBA1C, or the like. In implementations that include a glucose sensor, system 10 may be a fully closed-loop system operable in a manner to automatically monitor glucose level and deliver insulin, as appropriate, to maintain glucose level at desired levels. Information provided by any such sensors and/or sensor techniques may be communicated by system 10 using any one or more wired or wireless communication techniques.

In an implementation of the system 10, the electronic device 12 is provided in the form of a handheld device, such as a PDA or other handheld device. In this example, medical devices 30, 32 include at least one implantable or externally worn drug pump. In one embodiment, an insulin pump is configured to controllably deliver insulin to the user's body. In this embodiment, the insulin pump is also configured to wirelessly transmit information relating to insulin delivery to the handheld device 12. The handheld device 12 is configured to monitor insulin delivery by the pump, and may further be configured to determine and recommend insulin bolus amounts, carbohydrate intake, exercise, and the like to the user. The system 10 may be configured in this embodiment to provide for transmission of wireless information from the handheld device 12 to the insulin pump.

In a further embodiment, the handheld device 12 is configured to control insulin delivery to the user by determining insulin delivery commands and transmitting such commands to an insulin pump 32. The insulin pump, in turn, is configured to receive the insulin delivery commands from the handheld device 12, and to deliver insulin to the user according to the commands. The insulin pump, in this embodiment, may further process the insulin pump commands provided by the handheld unit 12. The system 10 will typically be configured in this embodiment to provide for transmission of wireless information from the insulin pump back to the handheld device 12 to thereby allow for monitoring of pump operation. The system 10 may further include one or more implanted and/or external sensors of the type described in the previous example.

Those skilled in the art will recognize other possible implementations of a fully closed-loop, semi closed-loop, or open loop diabetes control arrangement using at least some of the components of the system 10 illustrated in FIG. 1. For example, the electronic device 12 in one or more of the above examples may be provided in the form of a PDA, laptop, programmable cellular telephone, notebook or personal computer configured to communicate with one or more of the medical devices 30, 32, at least one of which is an insulin delivery system, to monitor and/or control the delivery of insulin to the user. In further embodiments, electronic device may include a communication port 22 in the form of a BLUETOOTH or other wireless transmitter/receiver, serial port or USB port, or other custom configured serial data communication port. In some embodiments, remote device 50, 52 is configured to communicate with the electronic device 12 and/or one or more of the medical devices 30, 32, to control and/or monitor insulin delivery to the patient, and/or to transfer one or more software programs and/or data to the electronic device 12. Remote device 50, 52 may take the form of a PC, PDA, programmable cellular telephone, laptop or notebook computer, handheld or otherwise portable device, and may reside in a caregiver's office or other remote location. In the various embodiments, communication between the remote device and any component of the system 10 may be accomplished via an intranet, internet (such as, for example, the world-wide-web), cellular, telephone modem, RF, USB connection cable, or other communication link 62. Any one or more internet protocols may be used in such communications. Additionally, any mobile content delivery system; e.g., Wi-Fi, WiMAX, BLUETOOTH, short message system (SMS), or other message scheme may be used to provide for communication between devices comprising the system 10.

FIG. 1 illustrates the components, and operation and control flow, of a typical closed-loop system. In the depicted embodiment, the system generally includes a sensor and a pump, and a controller module for receiving input from the sensor and for controlling the pump. In some embodiments, the sensor and/or pump is part of, or includes medical device 30, 32 (that is, medical device 30, 32 can be a pump or a sensor). In some embodiments, the controller module may be part of, or be integrated with, a sensor or a pump, or other medical devices 30, 32. In some embodiments, the controller module is part of, or comprises, electronic device 12. Thus, the controller module is depicted in the drawings as a handheld electronic device 12. Handheld controller 12 preferably has a user interface screen 20 to display information to the user and to request from the user the input of parameters and/or commands. Handheld controller 12 may further comprise a processor 14, and an input means 18, such as buttons or a touch screen, for the user to input and/or set parameters and commands to the system.

Handheld controller 12 includes a memory means 16 configured to store parameters and one or more algorithms that may be executed by processor 14. For example, memory means 16 may store one or more predetermined parameters or algorithms to evaluate glucose data, trends in that data, and future prediction models. A user may also input parameters using input 18 to provide patient-specific algorithms such as pumping patterns or algorithms for determining an amount of drug (i.e., insulin) to be delivered by an insulin delivery device (IDD), such as, for example, a pump. Input 18 may also be used to send commands or to bring up a menu of commands for the user to choose from. In some embodiments, these components (i.e., input, processor, and memory) comprise the control module of the present invention. The information may be displayed, for example, on display 20 of handheld controller 12, and user input may be received via input 18. In one embodiment, handheld controller 12 takes into account for both deliveries commanded by the controller as well as deliveries commanded by human input intended to correct or compensate for specific aspects not necessarily known to the controller. The components of the invention may cooperatively work together as a single device or separate physical devices.

In one embodiment, handheld controller 12 is provided to allow the patient to view via graphical display 20 his or her glucose levels and/or trends and to control the pump 32. Handheld controller 12 sends commands to operate pump 32, such as an automatic insulin basal rate or bolus amount. Handheld controller 12 may automatically send commands based on input from a sensor or may send commands after receiving user input via input 18 or input 34 on medical device 30, 32. In at least one embodiment, handheld controller 12 analyzes data from the sensor and/or pump, and/or communicates data and commands to them. In one embodiment, handheld controller 12 automatically sends the commands to the pump based on a sensor reading. Handheld controller 12 may also send commands to direct the pumping action of the pump. Handheld controller 12 sends and receives data to and from the sensor over a wired connection or wireless communication protocol 42. In another embodiment, data based on the reading is first provided to handheld controller 12 which analyzes the data and presents information to a user or a health care provider (such as, for example, using remote device 50, 52), wherein human input is required to generate the command. For example, handheld controller 12 may request an acknowledgment or feedback from the user before sending the commands, allowing the user to intervene in command selection or transmission. In a further embodiment, handheld controller 12 merely sends alerts or warnings to the user and allows the user to manually select and send the commands via the input 18 of handheld controller 12. In yet another embodiment handheld controller 12 manages commands originated by the control algorithm with or without user approval or intervention, and commands initiated by the user are independent of the control algorithm. The purpose of handheld controller 12 is to process sensor data in real-time and determine whether the glucose levels in a patient is too high or too low, and to provide a prediction of future glucose levels based upon sensor readings and the current basal rate and/or recent bolus injections.

In some embodiments, handheld controller 12 includes a means for calibrating the system, including, inputting at the device a finger stick glucose measurement or taking an actual blood sample to obtain a glucose measurement. The device may be integrated with a strip port so that a user may use the strip port to take a manual glucose level reading. The strip port includes a known calibration and is configured to take a blood reading to provide a value representative of a glucose level. The reading provided from the strip port is internally received at handheld controller 12 and compared to a value from the sensor to configure and/or calibrate the system.

In some embodiments, one or more of medical devices 30, 32 may be a sensor configured to measure a glucose level of a person and to send the measurement to handheld controller 12 for analysis. In some embodiments, the sensor is a glucose level monitor with a strip port for manually receiving a blood sample. In other embodiments, the sensor may be a continuous glucose monitoring (CGM) sensor that pierces and/or is held in place at the surface of a patient's skin to continuously monitor glucose levels in a person. In another embodiment, the CGM sensor (incorporated into medical device 30, 32) is attached to the surface of a patient's skin and includes a small sensor device that at least partially pierces the patient's skin and is located in the dermis to be in contact the interstitial fluid. The sensor device may also be held in place at the skin by a flexible patch. The CGM sensor is typically an analyte monitoring system that may also include a transmitter and/or receiver for transmitting sensor data to a separate device (such as, for example, an insulin pump or handheld electronic device 12). In some embodiments, the CGM sensor is mounted on the skin of a user's arm.

In the various embodiments described herein, an insulin device or pump delivers insulin to the patient through a small tube and cannula, also known as an "infusion set," percutaneously inserted into the patient's body. The insulin pump may be in the form of a medical pump, a small portable device (similar to a pager) worn on a belt or placed in a pocket, or it may be in the form of a patch pump that is affixed to the user's skin. In one embodiment, the pump is attached to the body by an adhesive patch and is normally worn under clothes. The pump includes a power supply, and is relatively small and of a low profile so that it can be hidden from view in a pocket or attached to the skin under a user's clothing.

The insulin pump typically has disposable and non-disposable components. The disposable components generally include a reservoir and cannula and optionally, an adhesive patch to hold the pump to the user's skin. The non-disposable/reusable components generally include the pumping electronics, transmitter and/or receiver, and pump mechanics (not shown). The pump and cannula may be part of the same physical device or comprise separate modules. The pump may also comprise a transmitter and/or receiver for transmitting and/or receiving a signal via connection 42 from handheld controller 12 so that it can be controlled remotely and can report pump-specific data to the controller. Alternatively, the pump may also be configured to communicate with one or more remote devices 50,52.

When provided as an integrated system, the components of system 10 work together to provide real-time continuous glucose monitoring and control of an insulin pump and to allow a user to take immediate corrective or preventative action when glucose levels are either too high or too low. Because the pump and sensor are miniaturized they may have very limited control panels, if any at all, and thus, in some embodiments, the sensor, pump, and controller 12 may all be integrated into a single device. In other embodiments, the sensor, pump, and controller 12 may be organized as two or three separate components. The components may be in wired communication, radio communication, fluid connection, or other communication protocol suitable for sending and receiving information between the components. Some components may be constructed to be reusable while others are disposable. For example, the cannula and the sensor may be disposable pieces apart from the pump and CGM sensor, which are both preferably reusable. The cannula and/or sensor will preferably be in fluid isolation from other components. Each component may have modular fittings so that the disposable components may interact with the non-disposable components while remaining in fluid isolation from each other.

Figure 2:
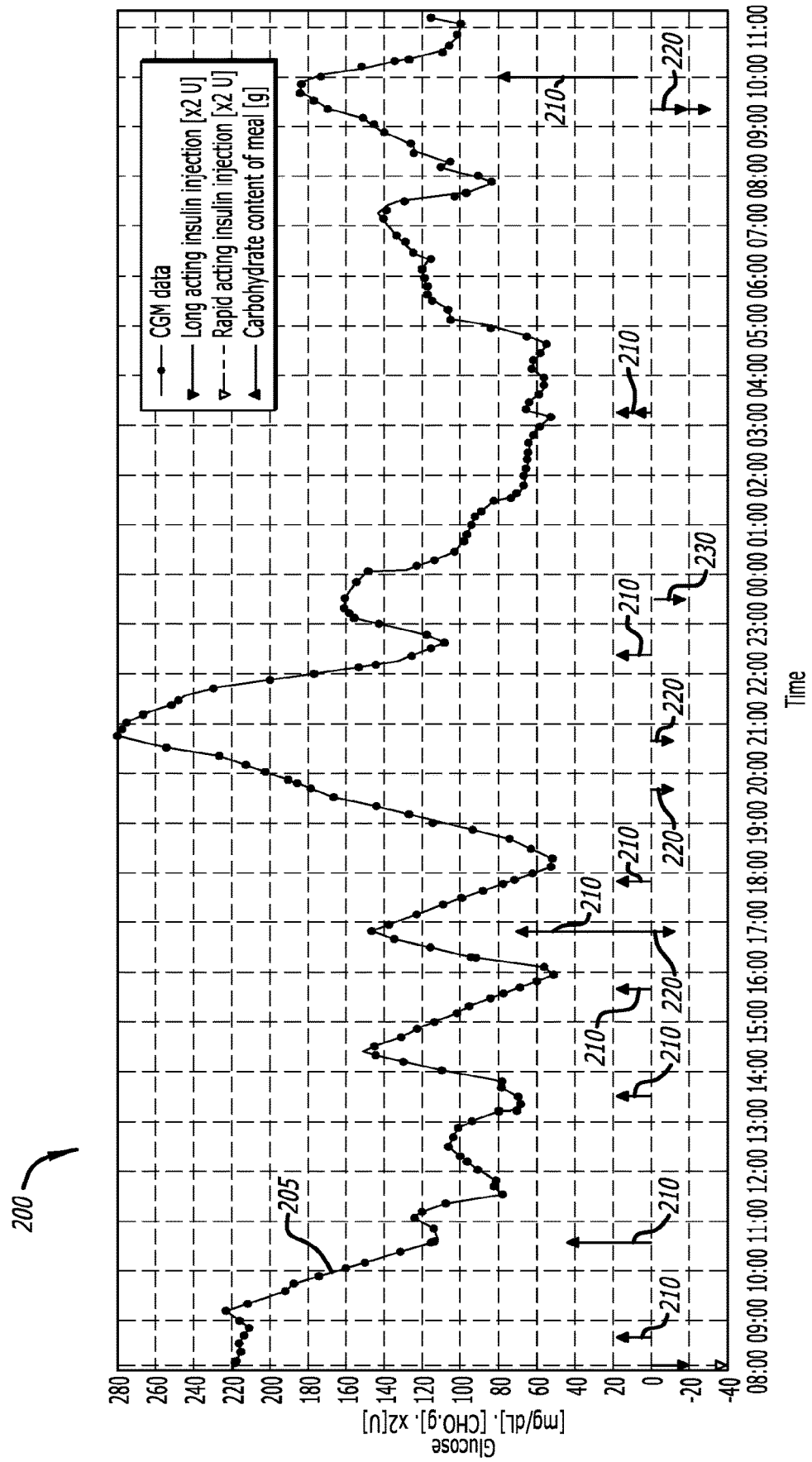
FIG. 2 is a graphical representation of a glucose profile showing glucose level measured using a CGM sensor as a function of time, and also showing the variation of the glucose level as function of carbohydrate intake and insulin administration.

FIG. 2 depicts a typical glucose absorption profile 200 for a user measured using a CGM sensor. The graph 205 plots the measured glucose level as a function of time. This profile shows the effect on glucose level of various actions, such as carbohydrate intake 210, and the delivery of rapid acting insulin 210 and long acting insulin 230.

Generally, the concentration of glucose in a person changes as a result of one or more external influences such as meals and exercise, and also changes resulting from various physiological mechanisms such as stress, illness, menstrual cycle and the like. In a person with diabetes, such changes can necessitate monitoring the person's glucose level and administering insulin or other glucose level altering drug, as needed to maintain the person's glucose level within desired ranges. In any of the above examples, the system 10 is thus configured to determine, based on some amount of user-specific information, an appropriate amount, type and/or timing of insulin or other glucose level altering drug to administer in order to maintain normal glucose levels without causing hypoglycemia or hyperglycemia.

In some embodiments, the system 10 is configured in a manner to control one or more external (such as, for example, subcutaneous, transcutaneous or transdermal) and/or implanted insulin pumps to automatically infuse or otherwise supply the appropriate amount and type of insulin to the user's body in the form of one or more insulin boluses. Such insulin bolus administration information may be or include, for example, insulin bolus quantity or quantities, bolus type, insulin bolus delivery time, times or intervals (such as, for example, single delivery, multiple discrete deliveries, and continuous delivery), and the like. Examples of user supplied information may be, for example but not limited to, user glucose concentration, information relating to a meal or snack that has been ingested, is being ingested, or is to be ingested sometime in the future, user exercise information, user stress information, user illness information, information relating to the user's menstrual cycle, and the like.

System 10 may also include a delivery mechanism for delivering controlled amounts of a drug; such as, for example, insulin, glucagon, incretin, or the like to pump 30, and/or offering an actionable therapy recommendation to the user via the display 20, such as, for example, ingesting carbohydrates, exercising, and the like. In other embodiments, the system 10 is configured in a manner to display or otherwise notify the user of the appropriate amount, type, and/or timing of insulin in the form of an insulin recommendation. In such embodiments, hardware and/or software forming part of the system 10 allows the user to accept the recommended insulin amount, type, and/or timing, or to reject it. If accepted, the system 10, in one embodiment, automatically infuses or otherwise provides the appropriate amount and type of insulin to the user's body in the form of one or more insulin boluses. If, on the other hand, the user rejects the insulin recommendation, hardware and/or software forming the system 10 allows the user to override the system 10 and manually enter insulin bolus quantity, type, and/or timing. The system 10 is then configured in a manner to automatically infuse or otherwise provide the user specified amount, type, and/or timing of insulin to the user's body in the form of one or more insulin boluses.

The appropriate amount and type of insulin corresponding to the insulin recommendation displayed by the system 10 may be manually injected into, or otherwise administered to, the patient's body. It will be understood, however, that the system 10 may additionally be configured in like manner to determine, recommend, and/or deliver other types of medication to a patient.

System 10 is operable to determine and either recommend or administer an appropriate amount of insulin or other glucose level lowering drug to the patient in the form of one or more insulin boluses. In determining such appropriate amounts of insulin, the system 10 requires at least some information relating to one or more external influences and/or various physiological mechanisms associated with the patient. For example, if the user is about to ingest, is ingesting, or has recently ingested, a meal or snack, the system 10 generally requires some information relating to the meal or snack to determine an appropriate amount, type and/or timing of one or more meal compensation boluses. When a person ingests food in the form of a meal or snack, the person's body reacts by absorbing glucose from the meal or snack over time. For purposes of this disclosure, any ingesting of food may be referred to hereinafter as a "meal," and the term "meal" therefore encompasses traditional meals, such as, for example, breakfast, lunch and dinner, as well as intermediate snacks, drinks, and the like.

The general shape of a glucose absorption profile for any person rises following ingestion of the meal, peaks at some measurable time following the meal, and then decreases thereafter. The speed, that is, the rate from beginning to completion, of any one glucose absorption profile typically varies for a person by meal composition, by meal type or time (such as, for example, breakfast, lunch, dinner, or snack) and/or according to one or more other factors, and may also vary from day-to-day under otherwise identical meal circumstances. Generally, the information relating to such meal intake information supplied by the user to the system 10 should contain, either explicitly or implicitly, an estimate of the carbohydrate content of the meal or snack, corresponding to the amount of carbohydrates that the user is about to ingest, is ingesting, or has recently ingested, as well as an estimate of the speed of overall glucose absorption from the meal by the user.

The estimate of the amount of carbohydrates that the user is about to ingest, is ingesting, or has recently ingested, may be provided by the patient in any of various forms. Examples include, but are not limited to, a direct estimate of carbohydrate weight (such as, for example, in units of grams or other convenient weight measure), an amount of carbohydrates relative to a reference amount (such as, for example, dimensionless), an estimate of meal or snack size (such as, for example, dimensionless), and an estimate of meal or snack size relative to a reference meal or snack size (such as, for example, dimensionless). Other forms of providing for user input of carbohydrate content of a meal or snack will occur to those skilled in the art, and any such other forms are contemplated by this disclosure.

The estimate of the speed of overall glucose absorption from the meal by the patient may likewise be provided by the patient in any of various forms. For example, for a specified value of the expected speed of overall glucose absorption, the glucose absorption profile captures the speed of the meal taken by the user. As another example, the speed of overall glucose absorption from the meal by the user also includes time duration between ingesting of the meal by a person and the peak glucose absorption of the meal by the user, which captures the duration of the meal taken by the user. The speed of overall glucose absorption may thus be expressed in the form of meal speed or duration. Examples of the expected speed of overall glucose absorption parameter in this case may include, but are not limited to, a compound parameter corresponding to an estimate of the meal speed or duration (such as, for example, units of time), a compound parameter corresponding to meal speed or duration relative to a reference meal speed or duration (such as, for example, dimensionless), or the like.

As another example of providing the estimate of the expected speed of overall glucose absorption parameter, the shape and duration of the glucose absorption profile may be mapped to the composition of the meal. Examples of the expected speed of overall glucose absorption parameter in this case may include, but are not limited to, an estimate of fat amount, protein amount and carbohydrate amount (such as, for example, in units of grams) in conjunction with a carbohydrate content estimate in the form of meal size or relative meal size, an estimate of fat amount, protein amount and carbohydrate amount relative to reference fat, protein and carbohydrate amounts in conjunction with a carbohydrate content estimate in the form of meal size or relative meal size, and an estimate of a total glycemic index of the meal or snack (such as, for example, dimensionless).

The term "total glycemic index" is defined for purposes of this disclosure as a parameter that ranks meals and snacks by the speed at which the meals or snacks cause the person's glucose level to rise. Thus, for example, a meal or snack having a low glycemic index produces a gradual rise in glucose level whereas a meal or snack having a high glycemic index produces a fast rise in glucose level. One exemplary measure of total glycemic index may be, but is not limited to, the ratio of carbohydrates absorbed from the meal and a reference value, such as, for example, derived from pure sugar or white bread, over a specified time period, such as, for example, 2 hours. Other forms of providing for user input of the expected overall speed of glucose absorption from the meal by the user, and/or for providing for user input of the expected shape and duration of the glucose absorption profile generally will occur to those skilled in the art, and any such other forms are contemplated by this disclosure.

Generally, the concentration of glucose in a person with diabetes changes as a result of one or more external influences such as meals and/or exercise, and may also change resulting from various physiological mechanisms such as stress, menstrual cycle and/or illness. In any of the above examples, the system 10 responds to the measured glucose level by determining the appropriate amount of insulin to administer in order to maintain normal glucose levels without causing hypoglycemia. In some embodiments, the system 10 is implemented as a discrete system with an appropriate sampling rate, which may be periodic, aperiodic or triggered, although other continuous systems or hybrid systems may be implemented as described above.

As one example of a diabetes control system, one or more software algorithms may include a collection of rule sets which use (1) glucose information, (2) insulin delivery information, and/or (3) subject inputs such as meal intake, exercise, stress, illness and/or other physiological properties to provide therapy, etc., to manage the user's glucose level. The rule sets are generally based on observations and clinical practices as well as mathematical models derived through or based on analysis of physiological mechanisms obtained from clinical studies. In the exemplary system, models of insulin pharmacokinetics and pharmacodynamics, glucose pharmacodynamics, meal absorption and exercise responses of individual patients are used to determine the timing and the amount of insulin to be delivered. A learning module may be provided to allow adjustment of the model parameters when the patient's overall performance metric degrades (such as, for example, adaptive algorithms, using Bayesian estimates, may be implemented). An analysis model may also be incorporated which oversees the learning to accept or reject learning. Adjustments are achieved utilizing heuristics, rules, formulae, minimization of cost function(s) or tables (such as, for example, gain scheduling).

Predictive models can be programmed into the processors of the system using appropriate embedded or inputted software to predict the outcome of adding a controlled amount of insulin or other drug to a user in terms of the an expected glucose value. The structures and parameters of the models define the anticipated behavior.

Any of a variety of controller design methodologies, such as PID systems, full state feedback systems with state estimators, output feedback systems, (Linear-Quadratic-Gaussian) controllers, LQR (Linear-Quadratic-Regulator) controllers, eigenvalue/eigenstructure controller systems, and the like, could be used to design algorithms to perform physiological control. They typically function by using information derived from physiological measurements and/or user inputs to determine the appropriate control action to use. While the simpler forms of such controllers use fixed parameters (and therefore rules) for computing the magnitude of control action, the parameters in more sophisticated forms of such controllers may use one or more dynamic parameters. In some embodiments, the one or more dynamic parameters take the form of one or more continuously or discretely adjustable gain values. In some embodiments, specific rules for adjusting such gains are defined on an individual basis, and, in other embodiments, on the basis of a patient population. In either case these rules will typically be derived according to one or more mathematical models. Such gains are scheduled according to one or more rule sets designed to cover the expected operating ranges in which operation is typically nonlinear and variable, thereby reducing sources of error.

Model based control systems, such as those utilizing model predictive control algorithms, can be constructed as a black box wherein equations and parameters have no strict analogs in physiology. Rather, such models may instead be representations that are adequate for the purpose of physiological control. The parameters are typically determined from measurements of physiological parameters such as glucose level, insulin concentration, and the like, and from physiological inputs such as food intake, alcohol intake, insulin doses, and the like, and also from physiological states such as stress level, exercise intensity and duration, menstrual cycle phase, and the like. These models are used to estimate current glucose level or to predict future glucose levels. Such models may also take into account unused insulin remaining in the blood after a bolus is given, for example, in anticipation of a meal. Such unused insulin will be variously described as unused, remaining, or "insulin on board" ("IOB").

Insulin therapy is derived by the system based on the model's ability to predict a user's glucose level for various inputs. Other modeling techniques may be additionally used including for example, but not limited to, building models from first principles.

As described above, system 10 includes an analyte monitor that continuously monitors the glucose levels in a user. The controller module is programmed with appropriate software and uses models as described above to predict the effect of carbohydrate ingestion and exercise, among other factors on the predicted level of glucose. Such a model must also take into account the amount of insulin remaining in the blood stream from a previous bolus or basal rate infusion when determining what or whether or not to provide a bolus of insulin.

In a system as described above, the controller is typically programmed to provide a "basal rate" of insulin delivery or administration. Such a basal rate is the rate of continuous supply of insulin by an insulin delivery device such as a pump that is used to maintain a desired glucose level in the user. Periodically, due to various events that affect the metabolism of a user, such as eating a meal or engaging in exercise, a "bolus" delivery of insulin is required. A "bolus" is defined as a specific amount of insulin that is required to raise the blood concentration of insulin to an effective level to counteract the affects of the ingestion of carbohydrates during a meal and also takes into account the affects of exercise on the glucose level of the user.

As described above, an analyte monitor may be used to continuously monitor the glucose level of a user. The controller is programmed with appropriate software and uses models as described above to predict the affect of carbohydrate ingestion and exercise, among other factors, on the predicted level of glucose of the user at a selected time. Such a model must also take into account the amount of insulin remaining in the blood stream from a previous bolus or basal rate infusion of insulin when determining whether or not to provide a bolus of insulin to the user.

Calibration error is a key fault mechanism for closed loop control on insulin delivery. Specifically, if the glucose signal being generated by a CGM sensor is calibrated such that the readings are higher than the actual glucose level, the closed loop controller will attempt to drive these reading into a normal glucose range, and may inadvertently drive the true, or actual, glucose level into a low glucose range. Detecting and mitigating calibration error is important for robust and safe closed loop control over the delivery of insulin.

In one embodiment of the invention, sensor signal anomalies are detected and the processor of the controller is programmed to adjust one or more closed loop system parameters appropriately to ensure that a safe glucose level is maintained. That is, the system may detect a problem but continue to operate with glucose control that is less than optimal. A little higher glucose level may be temporarily tolerated and is safer than an unsafe low glucose level.

Specifically, the CGM sensor generally has a "nominal sensitivity" value that best represents a single sensor batch. This 'nominal sensitivity" is determined at the factory before the sensor is shipped for use. Some manufacturers attach a sensor code to the sensor that indicates the factory, or nominal, sensitivity of the sensor. Just prior to the beginning of closed loop control (or any other appropriate time, such as just after calibration where a new sensor sensitivity value is determined), the system calculates the difference between the current (or most recent, or other sensitivity) and the nominal sensitivity, and if this difference exceeds a predetermined threshold (in the negative or positive direction or both) then a closed loop system parameter may be adjusted, such that the closed loop system will still maintain safe glucose control in the face of possible calibration error.

Figure 3:
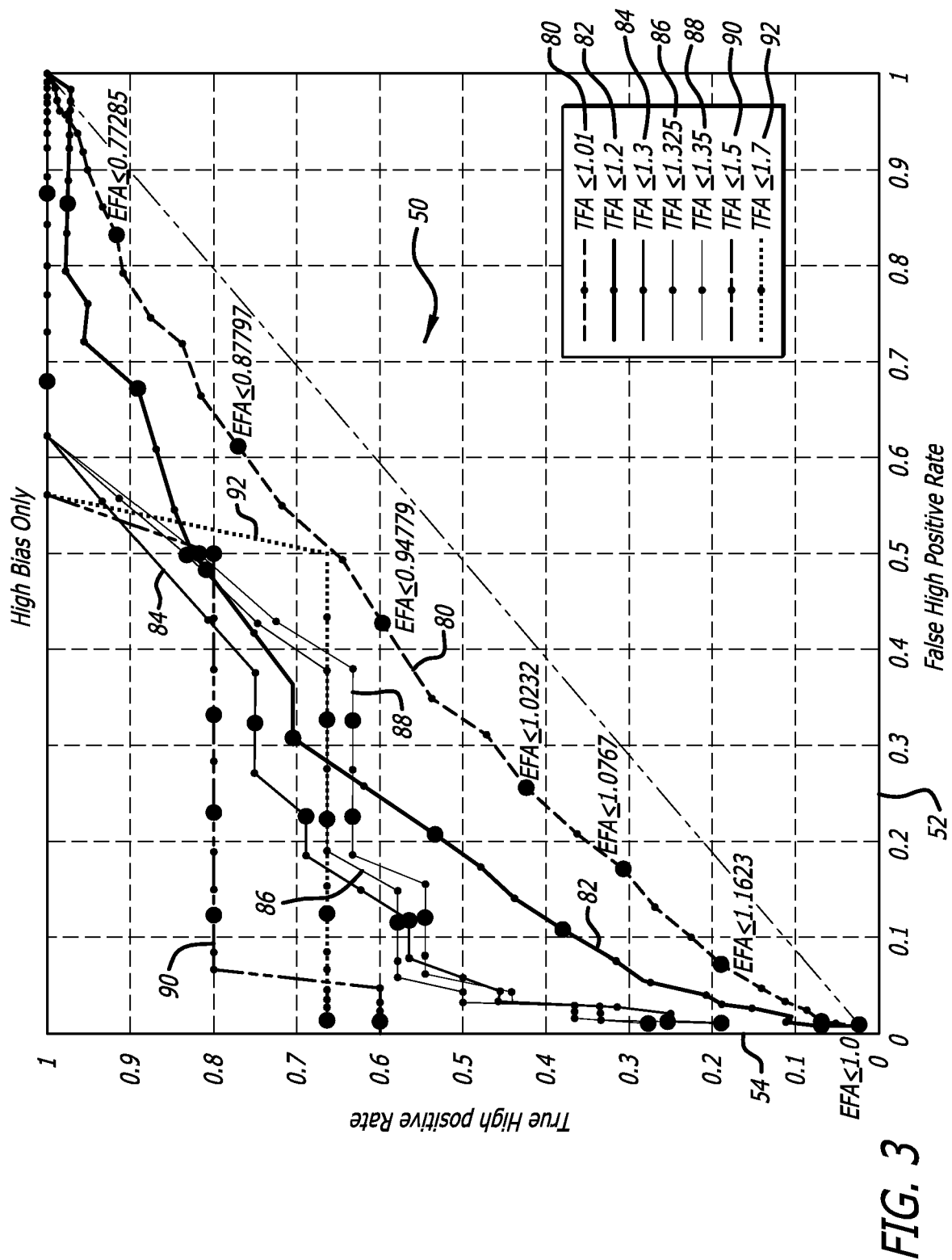
FIG. 3 presents a series of receiver operation curves useful for detecting positive calibration bias based on estimated fractional accuracy.

FIG. 3 shows a series of receiver operating characteristic ("ROC") curves 50 for detecting positive calibration bias. In the figure, true calibration bias is described in terms of True Fractional Accuracy ("TFA"). For example, TFA=1 implies perfect calibration, while TFA=1.2 implies a +20% calibration bias. The detector is based on Estimated Fractional Accuracy ("EFA") computed by taking the ratio of the latest calibration sensitivity to the sensor-code-based sensitivity (factory sensitivity). A high value of EFA implies a high likelihood of positive calibration bias. The x-axis 52 depicts the false alarm rate, while the y-axis 54 depicts the true detection rate. On the X-axis, a false alarm rate as close to zero is desired. While on the Y-axis, a true high positive rate as close to one as possible is desired. The straight dotted line between the 0,0 point and the 1,1 point on the graph indicates random accuracy and is undesirable. The various ROC curves 50 of FIG. 3 correspond to different levels of true positive bias thresholds as follows:

| Curve | Drawing Numeral |
|---|---|
| TFA ≤ 1.01 | 80 |
| TFA ≤ 1.2 | 82 |
| TFA ≤ 1.3 | 84 |
| TFA ≤ 1.325 | 86 |
| TFA ≤ 1.35 | 88 |
| TFA ≤ 1.5 | 90 |
| TFA ≤ 1.7 | 92 |

For example, the curve labeled with numeral 84 corresponds to a detector that attempts to detect positive calibration bias higher than +30%.

Figure 4:
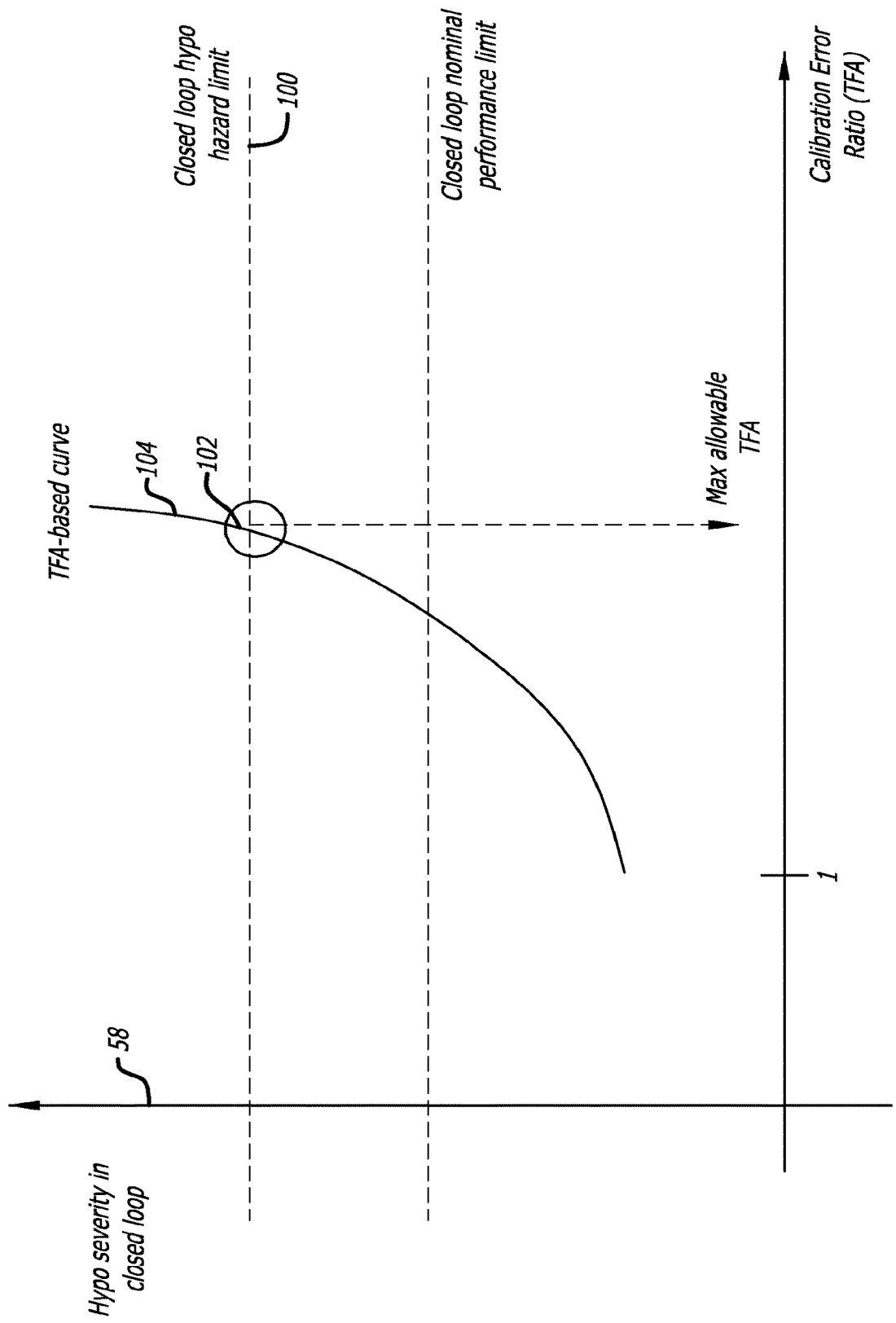
FIG. 4 is an example of determining the maximum allowable true calibration error in terms of hypoglycemic severity under closed loop delivery.

In one embodiment, the detector is programmed to detect when maximum tolerable safety limits of the user's glucose level are exceeded during operation of a closed loop system. An example of determining the maximum allowable true calibration error in terms of hypoglycemic severity under closed loop delivery is shown in FIG. 4, where hypoglycemic severity 58 is used as one metric to determine a maximum allowable true calibration error. The line indicated as "closed loop hypo (hypoglycemic) hazard limit 100 indicates the maximum severity tolerable. Projecting the point 102 at which the TFA line 104 crosses line 100 onto the x-axis indicates the maximum allowable calibration error ratio (TFA).

Returning to the notion of using a factory sensitivity check to adjust one or more closed loop parameters, one closed loop parameter adjustment would be to raise the upper limit of the controller's target glucose level when a significant positive calibration bias is suspected. In the event that calibration is not really biased positive, the resulting higher glucose would be tolerable for a short period of time, such as, for example, the remaining life of the sensor, or until the next calibration, but would be much safer in preventing inadvertent low actual glucose level.

Another closed loop parameter adjustment would be to increase the value of the covariance, or uncertainty, parameter associated with glucose measurement uncertainty (assuming that the controller was such as one to take this into account). In addition, the uncertainty parameter may only be associated with the scale of the glucose measurement—other uncertainty parameters associated with the scale of the glucose measurement, such as, for example, the higher derivatives of glucose measurement as a function of time or other variable, may not be adjusted, or adjusted differently. An obvious embodiment of adjusting variance is when a Kalman Filter framework is used to estimate present system states and predict these system states in the near future to adjust the variance. In such a framework, each state is being represented by a best estimate and its associated uncertainty level in the form of state variance.

In another embodiment, the results of the sensitivity comparison with the nominal sensitivity of the sensor may be used to determine if a glucose level ("BG") measurement is needed, such as, for example, at a time just before closed loop control was initiated, or periodically, for instance once per day. If the difference between the sensitivities exceeds a pre-determined threshold, then the BG reading would be requested by the system, and the resulting sensitivity could be used to further detect calibration error (and could be used to drive the previously described parameters, or perhaps even disallow closed loop control, or could be used for a new calibration or to trigger another BG request). One example of such a system is disclosed in U.S. patent application Ser. No. 12/202,302, filed Aug. 31, 2008, which is hereby incorporated by reference in its entirety.

As an example, consider the TFA≤1.2 curve 82 and the TFA≤1.3 84 curve 84 shown in FIG. 3. While the curve labeled with numeral 82 might be useful enough to adjust one or more control parameters, it may not have enough specificity to warrant a BG request. However, the curve labeled with numeral 84 is meant to detect a more severe positive bias, and may have enough specificity to warrant a BG request. Hence, different EFA-based detectors could be employed to induce different levels of behavior.

Figure 5:
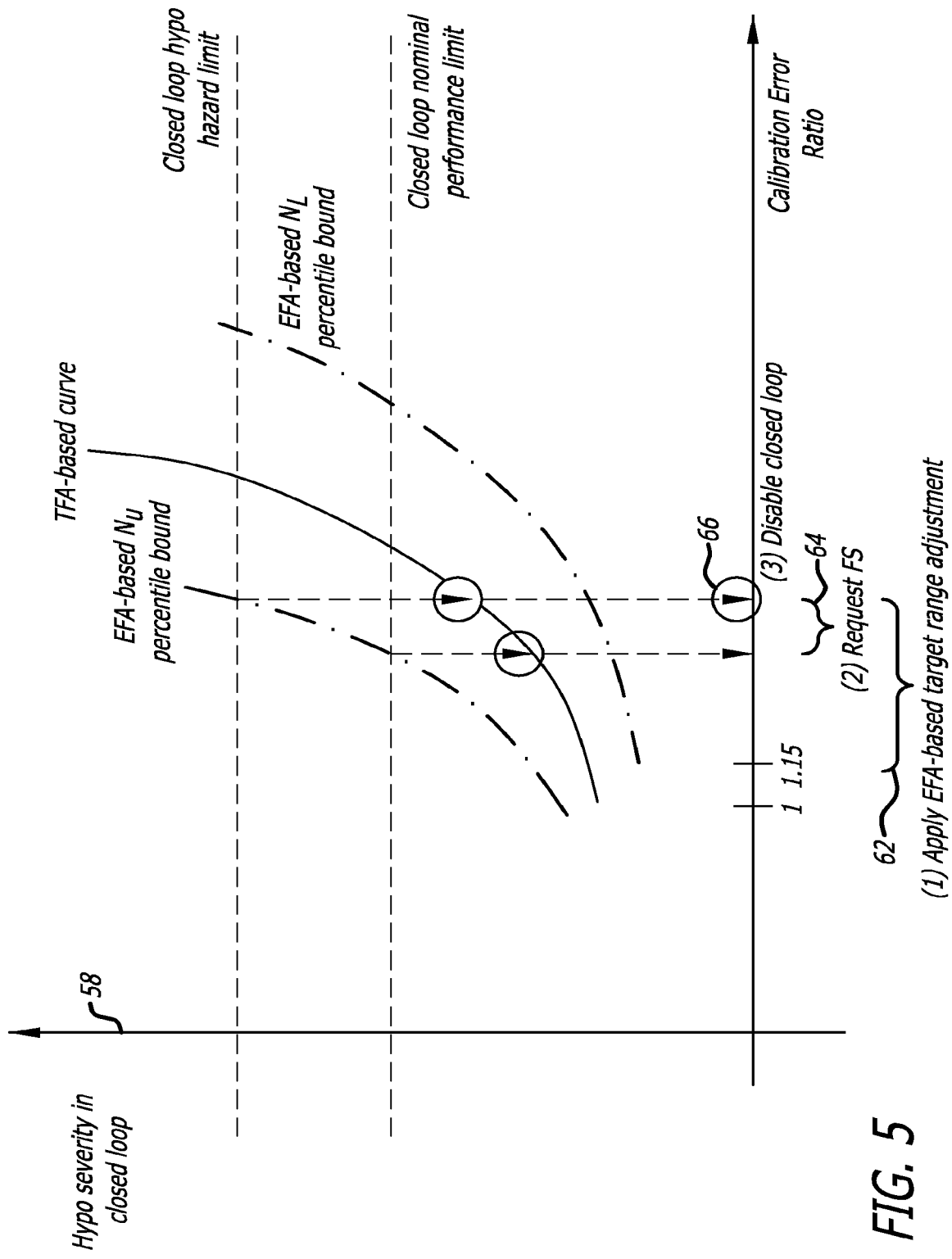
FIG. 5 shows the use of a single estimated fractional accuracy detector to determine different independent closed loop control parameter adjustments or trigger glucose reading requests.

In yet another embodiment, a single EFA-based detector and EFA value is used to determine several independent actions as shown in FIG. 5. This figure illustrates the use of a single EFA detector to determine different independent actions based on comparing the detector's value to a predetermined series of ranges. For example, when the EFA falls into a certain range of values shown by the bracket 62 (item (1) in FIG. 5 labeled "Apply EFA based target range adjustment"), the glucose target range can be adjusted to accommodate for mild calibration bias. Once the EFA falls into a certain range shown by the bracket 64 (item (2) in FIG. 5 labeled "Request FS"), a BG (by means of a Fingerstick ("FS") reading) may be requested. However, whenever the EFA exceeds a certain severe value 66 (item (3) in FIG. 5 labeled "Disable closed loop"), closed loop must be terminated/disabled.

Other sensor data quality detection methods may also be used to initiate closed loop control parameter adjustments or trigger BG reading requests. For example, the parameter adjustments may be designed to be functions of the sensitivity and nominal sensitivity. For instance, the uncertainty parameter may linearly increase proportional to increases in the difference between recently-measured sensitivity and nominal sensitivity. In addition, the detection of possible calibration error using recently-measured sensitivity and nominal sensitivity may be further enhanced by the logical addition of other factors, such as variability in previous immediate sensitivities.

Insulin delivery via pumps has been designed to approximate the physiological delivery of insulin. This is done through the use of fast-acting insulin that is delivered in two ways. Basal insulin is one or more low rates of insulin administration delivered throughout the day to account for normal fluctuations in glucose level that occur during the day. Bolus insulin is a comparatively large dose of insulin that is delivered over a relatively short period of time and is generally used to cover the carbohydrate load of a meal or to correct a high glucose level. Modern insulin pumps make use of both of these modes of insulin delivery.

Under closed-loop glucose control, the traditional distinction between basal and bolus glucose may become blurred. Under closed-loop control, insulin may be delivered at regular intervals, the timing and size of which may be based upon the determination of a control algorithm, utilizing the input provided by a continuous glucose sensor or monitor ("CGM"), targeted to maintain (or achieve) prescribed levels of glucose in a user. This moves dramatically away from the current standard of pre-programmed basal rates and intermittent user-selected bolus deliveries.

Closed-loop insulin systems that make use of standard or semi-custom insulin pumps or which incorporate times of open-loop insulin delivery may be required to utilize the existing paradigm of basal/bolus insulin delivery within their control approaches.

Many closed-loop algorithms in development are based upon the delivery of insulin boluses in regular intervals. In this case, the approach that has been widely used is to deactivate (or set to zero) the normally active pump basal rate of insulin delivery. This approach may be disadvantageous because any prolonged interruption of the closed-loop system (such as, for example, due to loss of RF communication between pump and controller) may lead to a substantial under delivery of insulin, since basal delivery would have been previously deactivated and commands for insulin boluses would not be received by the pump. Depending on the cause of cessation, the user may not receive an alert informing of this condition.

One exemplary approach to mitigate this risk in accordance with various embodiments of the invention is to leave a pre-programmed safe-level of basal delivery active during closed-loop control involving bolus delivery of insulin. With each issued bolus command by the algorithm, a command issuing a temporary basal rate of zero units/hour for a predetermined time is sent to the pump. It is envisioned that basal delivery would be re-suppressed after each successful closed-loop insulin delivery cycle. Thus, the expiration of the temporary basal delivery rate would serve as a watchdog that reactivates the pump's pre-programmed basal rate after a period without successful closed-loop control. This suppresses basal rate delivery of insulin during closed-loop operation and reduces the risk that in the event of unexpected cessation of closed loop operation that the user would be left without active insulin delivery.

In other embodiments, the temporary basal rate delivery may be set to some other (non-zero value) as determined by the control algorithm. In still other embodiments, the duration of the temporary basal rate could be some value other than a single closed-loop cycle, such as, for example, duration of the temporary basal rate could be for two, three or more closed-loop cycles.

In still other embodiments, the duration of the temporary basal rate may be determined based upon the amount of insulin delivered in the preceding closed-loop cycle or may be based upon the level of insulin onboard (IOB). For example, if the user has a high-level of IOB, the algorithm may issue a temporary basal rate of zero units/hour (or similar) that lasts for a longer time than if the user has low IOB.

In yet another embodiment, the duration of the temporary basal rate may be determined based upon the amount of insulin delivered in the preceding closed-loop cycle or could be based upon the level of insulin onboard (IOB) in conjunction with the knowledge of the pre-programmed basal rate. For example, if the user has a high level of IOB, and the pre-programmed basal rate is judged to be high, the algorithm could issue a temporary basal rate of some duration of zero units/hour (or some level of insulin delivery that is lower than the pre-programmed basal rate). Similarly, if the user has a lower level of IOB, and the pre-programmed basal rate is judged to be low, the algorithm may issue a temporary basal rate of some duration of non-zero units/hour higher than the pre-programmed basal rate.

In the present state of artificial pancreas research, investigators typically choose to use insulin as a means of controlling a person's glucose level. Defining this process in terms of control theory as it is understood by those skilled in the art, this control action is single directional in that only a non-negative insulin dosage can be administered, and since it can only decrease glucose level, there is usually no safety mechanism to determine the lowest insulin delivery rate under a closed loop delivery system other than a zero rate. At best, there may be a constant nonzero minimum delivery rate.

The need for a safety mechanism that governs a non-zero and possibly time-varying minimum basal rate of insulin delivery arises from the coupling effect of a negative calibration bias in the continuous glucose monitor ("CGM") component that will falsely under represent glucose to the controller.

Since a negative calibration bias of the CGM causes the controller to perceive that the user has a lower glucose level than is actually present, the controller determines a lower amount of insulin than the user may require to control the user's actual glucose level. At the extreme, the controller may even decide to halt insulin delivery. While this action is justified when the user is actually experiencing hypoglycemia, it can result in undetected and uncontrolled hyperglycemia when coupled with a negative calibration bias.

In one embodiment of the invention, the processor of the controller is programmed using appropriate software or hardware commands to function in a manner so as to provide a safety mechanism that accounts for the coupling of a negative calibration bias and the hazard of hyperglycemia due to delivering a reduced amount of insulin, not delivering insulin, or delivering an opposite action such as glucagon to the user's bloodstream.

Model-based control allows for a rational weighting between observed data (such as, for example, measurement data obtained from CGM sensors, user-announced meals, and the like) and the best estimate of the true values of glucose levels based on an internal model tracked by the system.

Along the same lines, a model that keeps track of the user's typical insulin history in the various compartments as followed by the model can be used to mitigate against instances where a naïve calculation of insulin delivery based on the CGM value would result in a very low or no delivery over an extended period of time.

In another embodiment, a simple model is used to track the insulin-on-board (IOB) of the user such that a pattern is established. This pattern may be based either on online user data, that is data generated in real time, or data that has been collected from a user over time, offline collection of data for many users, or a combination thereof, such that regardless of what the glucose-based measurements indicate, the system will attempt to mitigate the hazards of insulin deprivation. Diurnal pattern or other patterns of this IOB history could be identified using available data.

Following the various model-based measures of insulin, either in terms of specific insulin compartment of a model, a series of insulin compartments of a model, or IOB, the programming of the processor embodying the safety mechanism attempts to determine the maximum duration that the model can allow the user to have a low amount of insulin. Four examples of the use of such a safety mechanism in accordance with the various embodiments of the invention are described below:

1. Assume one low glucose threshold has been exceeded. Then, depending on the aggressiveness of the safety mechanism, that is, the sensitivity of the mechanism and the trigger points at which the mechanism will determine that an action must be taken, the amount of insulin as computed by the system prior to taking into account for this mechanism will be bounded from below by this safety mechanism. For example, assume that due to a negative CGM calibration bias, the controller (without the safety mechanism of aspects of this invention) has been delivering a steady rate of 0.05 units of insulin (per hour). Now also assume that the IOB-based safety mechanism is activated, and the safety mechanism determines that the amount of IOB has been lower than a pre-determined threshold for a pre-determined amount of time. Then, the safety mechanism overrides the delivery rate and commands the pump to increase the delivery rate to a pre-determined amount, such as, for example, 0.15 units (per hour) for a pre-determined amount of time, until the safety mechanism determines that the IOB has returned to a minimum safety limit.

2. In yet another embodiment, the safety mechanism programmed into the processor does not necessarily ensure a certain minimum IOB by intervening in the insulin command. Instead, the safety mechanism issues a CGM validity confirmation. Examples of such a confirmation include providing the user with a request to recalibrate the CGM system or a requesting the user to obtain a glucose level measurement using an alternate device. If the CGM system used for closed loop feedback is significantly biased, a recalibration or a confirmation from an alternate device may reveal the source of the low IOB.

3. In yet another embodiment, different levels of threshold are used to determine a combination of the two types of action previously described. The safety mechanism may initially decide to ensure that a certain minimum amount of insulin is delivered, and that delivery minimum may vary over time. During this time, the system may or may not alert the user that the user is in a hypoglycemic state. Beyond this point, the safety mechanism may determine that the risk mitigation itself may be too risky to continue in the event that the user really is in hypoglycemia. Before the risk approaches a tolerable limit, the safety mechanism may opt to follow the second path described, in that either a CGM recalibration is requested, or an alternate measurement is requested. Otherwise, the closed loop system will terminate operation.

4. In yet another embodiment, the same limitations can be extended to the case when a bidirectional means of controlling glucose is employed. One example is the use of insulin to reduce glucose and glucagon to induce the liver to release glucose (thereby making more glucose available in the circulation). If the system determines either to deliver less insulin, halts insulin delivery, or delivers glucagon contrary to the safety mechanism described herein, the safety mechanism can react in the manner described in examples 1 through 3 above.

A negatively biased CGM system used for closed loop operation typically results in a reduced or discontinued insulin delivery. Even worse, a closed loop system employing a bidirectional means of control (for example, in a system using insulin to lower glucose level and using glucagon to raise glucose level) may even force the patient into further hyperglycemia with the release of glucagon. The safety mechanism is programmed appropriately to ensure that the safety mechanism does not unnecessarily increase the acute hazard of hypoglycemia while attempting to protect the user from hyperglycemia.

Prior to the start of closed-loop insulin delivery, it is likely that a reference glucose level measurement will be obtained by the patient in order to ensure that the glucose sensor is functioning properly (such as, for example, appropriately calibrated to reflect glucose levels). This reference glucose level measurement may be prompted by the closed-loop software, allowing for an automated determination of the proper functioning of the sensor, or may be performed procedurally, where a user obtains a reference glucose level measurement (such as, for example, a fingerstick glucose reading) and makes a determination of whether or not the sensor is functioning properly based upon defined rules (such as, for example, a table of acceptable ranges of sensor glucose reading for a given reference glucose level). This step may be required by the closed-loop software in order to initiate a closed-loop session or may be used to inform the determination of the aggressiveness or set-point of the closed loop algorithm. An example of such a system is disclosed in U.S. patent application Ser. No. 12/202,302 filed Aug. 31, 2008, now U.S. Patent Application Publication No. 2010/0057041, which is hereby incorporated herein by reference in its entirety.

As a matter of safety, it may be desirable to have an asymmetrical range for acceptable CGM bias, as determined by comparison with the reference glucose level measurement, prior to the start of closed-loop insulin delivery. For example, clinical or simulated data of the control algorithm can be used to determine the level of high calibration bias that yields acceptable glucose level control. Using these data, an acceptable level of high calibration bias under which closed-loop control should be activated can be determined (such as, for example, +50%). If the calibration bias is higher than this level, the user may be directed to perform a manual (forced) calibration prior to initiating closed-loop control, or some other output could be initiated. In a similar manner, if a reference glucose level measurement indicates that the CGM is biased lower than a certain level, the user may be directed to perform a manual (forced) calibration prior to initiating closed-loop control. As used herein, "manual calibration" is a calibration of the glucose monitor or sensor that is initiated by the user as opposed to being initiated by the controller requesting the patient to conduct a calibration.

The levels of high and low bias that are deemed acceptable for the initiation of closed-loop control are dependent on the nature of the closed-loop algorithm. Algorithms can be designed such that they are robust to high calibration bias, such as through imposed limits on the rates of insulin delivery or through other approaches.

Low calibration bias, however, presents a unique challenge. If the low bias is due to an anomalous depressed sensor output, such as, for example, due to early sensitivity attenuation ("ESA") or dropout behavior instead of a calibration that results in a low biased reading, performing a manual calibration may not be desirable as subsequent recovery from the depressed sensor output may result in very high sensor bias, potentially leading to dangerous levels of hypoglycemia.

It may therefore be desirable to allow closed-loop to begin under conditions of large level of low calibration bias rather than require a manual calibration prior to initiating the closed-loop session. This may be true despite the additional hyperglycemic exposure to which the user will likely be subjected due to the low sensor bias because of the greater relative risk of hypoglycemia which may occur due to recovery from an anomalously depressed output. Alternatively, manual calibrations performed with large low calibration bias may only be accepted by the system under certain conditions. For example, manual calibrations performed during a low bias state may require a follow up measurement at a later time to confirm that the manual calibration corrected the bias.

Accordingly, the controller may be programmed to accept an asymmetrical range for acceptable CGM bias (as measured by reference BG measurement) prior to starting of closed-loop. The processor may also be programmed to require manual (forced) calibrations outside of this range in order to initiate a closed-loop session.

This approach of these embodiments may also be extended to CGM devices used outside of closed-loop insulin delivery. That is, manual calibrations may only be accepted by the system if the existing bias (as determined by a reference glucose level measurement) is outside of some asymmetric range.

In a further embodiment of the invention, new safety features are provided to allow a continuous glucose monitor ("CGM") condition or conditions to terminate pump delivery, specifically terminating extended bolus delivery, programmed basal rate delivery, and temporary basal rate delivery (if it is higher than the programmed basal delivery rate) or to reduce future basal delivery rates. These safety features can be implemented in open loop, semi-closed loop, or closed loop systems.

The embodiments of the invention incorporating such safety features are particularly useful for insulin deliveries that are not instantaneous or on-demand (such as, for example, a one time delivery that lasts only a few minutes), like a normal meal bolus of insulin. There are several insulin delivery modes that are not instantaneous, or are scheduled for longer term insulin deliver, such as, for example, programmed basal rate insulin delivery, temporary basal rate insulin delivery, and extended bolus insulin deliver. Programmed basal rate insulin delivery is the basal rate of insulin delivery that is typically delivered throughout the day. Temporary basal rate insulin delivery can be programmed to override the programmed basal insulin delivery rate, and a temporary basal rate insulin delivery is typically carried out when there is a break in a user's daily routine. For example, if a pump user who usually works outdoors for some reason has a classroom training one afternoon, he may choose to change his basal insulin delivery rate for that afternoon. Alternatively, the user may instead program a temporary basal rate lasting several hours in duration. After this duration is reached, the pump returns to the programmed basal rate of insulin delivery. Additionally, an extended bolus is a bolus that is scheduled over a period of time instead of an instantaneous bolus. Typically the pump user gives a normal bolus (or instantaneous bolus) for a single meal that is consumed at one time. If the user snacks throughout the afternoon (such as, for example, at a social gathering), the user may program the pump to deliver an extended bolus of insulin is delivered over several hours. In addition, an extended bolus of insulin is also used when there is higher fat/protein content in the food that is to be ingested. Higher fat content in a meal will usually delay the onset of the glucose spike in the user's glucose level profile due to the meal. In this case, the pump user may choose to deliver an extended food bolus over a selected period of time, such as, for example, the next 30 to 90 minutes, instead of programming the bolus to be given all at once at, say, 15 minutes before the meal.

In a combined CGM and pump device, an extended bolus or temporary basal (when greater than the programmed basal rate) could be terminated based on the condition of the current CGM glucose level measurements. For example, if the current IOB and the current CGM measurements indicate the user may be carbohydrate deficient already or trending towards being carbohydrate deficient, then for safety reasons, such as, for example, to prevent hypoglycemia, the pump may automatically terminate or suspend further delivery of the programmed extended bolus delivery of insulin. The decision to terminate may be arrived at by the processor by programming the processor to consider one or more of the following parameters:

IOB—in conjunction with a CGM reading, whether the user is in a carbohydrate deficient state or not Current CGM reading—in conjunction with IOB, whether the user is in a carbohydrate deficient state or not Current CGM rate of change—is the trend of the measured glucose level going up or going down and how fast is the trend changing?

Projected BG Threshold—how soon will the user cross the low BG threshold, that is, what is the estimated time until the user's glucose level crosses the threshold and places the user at risk of hypoglycemia?

Low BG Threshold—once the user crosses the low BG threshold, how much time is estimated, based on the user's IOB, current glucose level and insulin and glucose history, remains before the user is in a dangerous hypoglycemic state?

Has the processor annunciated any alarms to the user indicating that the user's glucose level is dangerously low, and has the user taken any action to resolve the alarm, or has the user ignored the alarm?

In addition to terminating an extended bolus or a temporary basal rate insulin delivery that is higher than programmed basal before the scheduled termination time, the system may choose to terminate or suspend a programmed basal delivery by setting a temporary basal of zero, or the processor may issue a command to reduce the future basal delivery rate by setting a temporary basal rate to be less than the current programmed basal delivery rate for a selected duration that is either pre-defined, calculated, or defined by the user to allow the user to recover from the carbohydrate deficient state.

How much basal reduction and/or the duration of the basal reduction (by suspending basal rate completely by setting the temporary basal rate to zero, or by reducing future basal rate to lower than programmed basal rate) can be calculated by the processor to determine the amount of the insulin reduction needed to recover from the carbohydrate deficient state. In one embodiment, this calculation is performed by the processor executing suitable programming commands and using a stored value for the user's insulin sensitivity factor ("ISF") value that is typically available for user's undergoing insulin pump therapy to treat their diabetes.

For example, the IOB value for the user, the current CGM glucose measurement, and the user's ISF allow the processor of the controller or pump to calculate how much extra insulin is in the body than the amount needed to metabolize the amount of carbohydrates ingested by the user at the last snack or meal. This calculated excess is the total insulin reduction needed to resolve the carbohydrate deficient state.

The processor also analyzes the CGM glucose measurement value and the presence or absence of a currently pending low glucose level alarm or projected low glucose level alarm to determine whether to command a large reduction in insulin delivery or a complete suspension of basal insulin delivery for a short period of time is warranted to avoid an imminent state of hypoglycemia. Depending on the thresholds programmed into the processor concerning the user's glucose level, alarm state and IOB, the processor may be programmed to take either an aggressive intervention, or a less aggressive intervention in ceasing or altering the current basal rate. For example, the processor may be controlled by a software embodied CGM projected alarm algorithm that may project the time at with a low glucose level will be reached, and the processor may then use this value as the duration of the temporary basal rate. With this value, the amount of insulin delivery reduction needed to resolve the user's carbohydrate deficient state may be calculated. The processor then sends the appropriate command to the pump to either cease basal rate insulin delivery or reduce the rate of insulin delivery so that over time the user's glucose level profile trends away from hypoglycemia towards euglycemia at an acceptable rate.

In some cases, a more gradual reduction in basal insulin delivery rate may be preferred if the current CGM glucose level measurement, when compared to the IOB, stored insulin history and projected glucose level profile by the processor, indicates that no imminent hypoglycemia will occur, and that a more conservative intervention of the current basal delivery rate can be used to bring the user's glucose level profile into an acceptable range. Using the data available to it, the processor can be programmed to determine the percentage reduction in insulin deliver that is gradual enough to reach the desired level, and then back-calculate the duration of delivery at the selected rate needed to reach the total insulin reduction desired.

Alternatively, in a semi-closed loop system, or a fully closed loop system that is in an open loop state, the closed loop predictive model may still inform the user of the amount and duration of the basal rate.

Furthermore, the system may inform the user that a carbohydrate deficient state has been reached and the recommend to the user the number of carbohydrates needed to metabolize the extra insulin that the system has determined is present. The processor may be programmed to not only determine a course of action of stopping or slowing insulin delivery, but the processor may also recommend to the user that the user simply consume extra carbohydrates to cover the extra insulin in the user's body.

In another embodiment, the controller may be programmed to terminate an extended bolus delivery or terminate or reduce future basal insulin delivery when both IOB or CGM glucose level measurements are available or when certain CGM events occur (such as, for example, where the user's glucose level is trending towards hypoglycemia) or when certain pump events occur (such as, for example, where an extended bolus delivery, or where the processor had determined to employ a temporary basal delivery rate that is less than the programmed basal delivery rate) or a combination of these events and glucose level conditions.

In addition, with the availability of CGM and IOB readings, a safety limit on the possible IOB level can be implemented by the programming of the processor to provide an additional bolus safeguard that prevents the user from over-dosing insulin using bolus deliveries of insulin. For example, this function can prevent the user from making any correction bolus that would raise the user's projected IOB over the safety IOB limit that is calculated from the current CGM glucose level measurement so that the user avoids entry into a carbohydrate deficient state. Furthermore, the processor can be programmed so that the user can deliver a food bolus only in conjunction with a meal, the amount of the bolus allowed to be given dependent on whether the bolus and carbohydrate amount of the meal will raise the IOB over the safety IOB limit.

The various embodiments of the present invention, embodied in suitable program commands executed by the processor of the controller or pump, provide new safety features that previous generations of insulin pumps are unable to provide because they do not have access to CGM glucose level measurements. In the past, an extended bolus insulin delivery, temporary basal rate insulin deliver, or programmed basal rate insulin delivery could only be terminated early through manual intervention by the user. However, given the integration of the CGM, pump and controller, the system can be programmed to implement auto-termination as an additional safety mechanism in case certain CGM glucose level conditions are reached.

The integration of CGM allows better monitoring of excess insulin and can provide the user with more options to recover from a carbohydrate deficient state than just eating more carbohydrates. One undesirable side effect of such a strategy is that is often leads to unwanted weight gain. As described above, programming the processor of the controller or pump in an integrated system provides for automatically or semi-automatically reducing a future basal delivery rate of insulin using the temporary basal functions embodied in the software and hardware of the present invention to improve safety and compliance of insulin pump use.

While the invention has been described in connection with what is presently considered to be the most practical and preferred embodiments, it is to be understood that the invention is not to be limited to the disclosed embodiments and elements, but, to the contrary, is intended to cover various modifications, combinations of features, equivalent arrangements, and equivalent elements included within the spirit and scope of the appended claims. Thus, it is intended that the present invention covers modifications and variations of the examples shown.

What is claimed is:

1. A system, comprising:
a glucose monitor comprising:
a glucose sensor comprising a first portion configured to be arranged above a skin surface of a user, and a second portion configured to be arranged below the skin surface and in contact with an interstitial fluid of the user to provide signals representative of glucose levels, and
a transmitter in communication with the glucose sensor, wherein the transmitter is configured to wirelessly transmit the signals representative of glucose levels; and
an insulin pump controller in data communication with the glucose monitor to receive the signals representative of glucose levels, wherein the insulin pump controller is configured to provide control signals to an insulin pump, and wherein the insulin pump controller comprises a processor and a memory that stores programming configured to cause the processor to:
determine a difference between a factory sensitivity of the glucose sensor and a sensitivity of the glucose sensor in operation, and
provide a control signal to the insulin pump to terminate insulin delivery in response to determining that the difference between the factory sensitivity of the glucose sensor and the sensitivity of the glucose sensor in operation exceeds a predetermined threshold.

2. The system of claim 1, wherein the insulin pump controller is a semi-closed loop controller.

3. The system of claim 1, wherein the insulin pump controller is a fully closed loop controller.

4. The system of claim 1, further comprising an electronic device in wireless communication with the glucose monitor, wherein the electronic device is configured to communicate with an insulin pump.

5. The system of claim 4, wherein the electronic device comprises the insulin pump controller.

6. The system of claim 1, further comprising an insulin pump in communication with the insulin pump controller and with the glucose monitor, wherein the insulin pump is configured to administer insulin to the user based on the control signals from the insulin pump controller.

7. The system of claim 6, wherein the insulin pump comprises the insulin pump controller.

8. The system of claim 6, further comprising an electronic device in communication with the glucose monitor and with the insulin pump, wherein the electronic device comprises a display configured to display information corresponding to the glucose levels.

9. The system of claim 1, wherein the programming is further configured to cause the processor to prompt a user to enter a blood glucose measurement in response to the difference between the factory sensitivity and the sensitivity of the glucose sensor in operation exceeding a second predetermined threshold.

10. A system, comprising:
a glucose monitor comprising:
a glucose sensor comprising a first portion configured to be arranged above a skin surface of a user, and a second portion configured to be arranged below the skin surface and in contact with an interstitial fluid of the user to provide signals representative of glucose levels, and
a transmitter in communication with the glucose sensor, wherein the transmitter is configured to wirelessly transmit the signals representative of glucose levels; and an insulin pump controller in data communication with the glucose monitor to receive the signals representative of glucose levels, wherein the insulin pump controller is configured to provide control signals to an insulin pump, and wherein the insulin pump controller comprises a processor and a memory that stores programming configured to cause the processor to:
determine a difference between a factory sensitivity of the glucose sensor and a sensitivity of the glucose sensor in operation,
adjust a calibration correction factor to be applied to the signals representative of glucose levels when the difference between the factory sensitivity and the sensitivity of the glucose sensor in operation exceeds a predetermined threshold, and
communicate a control signal to the insulin pump to terminate insulin delivery based on the difference between the factory sensitivity and the sensitivity of the glucose sensor in operation.

11. The system of claim 10, wherein the insulin pump controller is a semi-closed loop controller.

12. The system of claim 10, wherein the insulin pump controller is a fully closed loop controller.

13. The system of claim 10, further comprising an electronic device in wireless communication with the glucose monitor, wherein the electronic device is configured to communicate with an insulin pump.

14. The system of claim 13, wherein the electronic device comprises the insulin pump controller.

15. The system of claim 10, further comprising an insulin pump in communication with the insulin pump controller and with the glucose monitor, wherein the insulin pump is configured to administer insulin to the user based on the control signals from the insulin pump controller.

16. The system of claim 15, wherein the insulin pump comprises the insulin pump controller.

17. The system of claim 15, further comprising an electronic device in communication with the glucose monitor and with the insulin pump, wherein the electronic device comprises a display configured to display information corresponding to the glucose levels.

18. A method, comprising:
providing signals representative of glucose levels by a glucose sensor of a glucose monitor, wherein a first portion of the glucose sensor is configured to be placed above a skin surface of a user, and wherein a second portion of the glucose sensor is configured to be placed below the skin surface and in contact with an interstitial fluid of the user;

transmitting, via a wireless communication protocol, the signals representative of glucose levels to an insulin pump controller in data communication with the glucose monitor, wherein the insulin pump controller is configured to provide control signals to an insulin pump;

determining, by the insulin pump controller, a difference between a factory sensitivity of the glucose sensor and a sensitivity of the glucose sensor in operation;

adjusting a calibration correction factor to be applied to the signals representative of glucose levels based on the difference between the factory sensitivity and the sensitivity of the glucose sensor in operation; and communicating a control signal to the insulin pump to terminate insulin delivery based on the difference between the factory sensitivity and the sensitivity of the glucose sensor in operation.

19. The method of claim 18, further comprising:
determining estimated glucose levels based on the signals representative of the glucose levels and the calibration correction factor.

20. The method of claim 18, further comprising:
communicating, from the insulin pump controller to an insulin pump in communication with the insulin pump controller, a control signal to terminate insulin delivery when the difference between the factory sensitivity and the sensitivity of the glucose sensor in operation exceeds a predetermined threshold.

* * * * *

UNITED STATES PATENT AND TRADEMARK OFFICE
CERTIFICATE OF CORRECTION

| | | |
|---|---|---|
| PATENT NO. | : 12,268,844 B2 | Page 1 of 1 |
| APPLICATION NO. | : 17/513487 | |
| DATED | : April 8, 2025 | |
| INVENTOR(S) | : Budiman et al. | |

It is certified that error appears in the above-identified patent and that said Letters Patent is hereby corrected as shown below:

On the Title Page

Column 1, Item (60), under "Related U.S. Application Data", Line 1, delete "(60)" and insert -- (63) --, therefor.

In the Claims

In Column 28, Claim 10, Lines 21-28, delete "an insulin pump controller …….. processor to:" and insert the same on Line 22, as a new sub-point.

Signed and Sealed this
Tenth Day of June, 2025

Coke Morgan Stewart
*Acting Director of the United States Patent and Trademark Office*